(12) United States Patent
Riesinger

(10) Patent No.: US 9,907,708 B2
(45) Date of Patent: Mar. 6, 2018

(54) WOUND CARE ARTICLE FOR EXTRACTION AND CONTROL OF WOUND FLUIDS

(71) Applicant: BSN medical GmbH, Hamburg (DE)

(72) Inventor: Birgit Riesinger, Munster (DE)

(73) Assignee: BSN MEDICAL HOLDING GMBH, Hamburg (DE)

( * ) Notice: Subject to any disclaimer, the term of this patent is extended or adjusted under 35 U.S.C. 154(b) by 610 days.

(21) Appl. No.: 14/218,237

(22) Filed: Mar. 18, 2014

(65) Prior Publication Data

US 2014/0296813 A1 Oct. 2, 2014

Related U.S. Application Data

(63) Continuation of application No. 12/443,989, filed as application No. PCT/EP2007/060304 on Sep. 28, 2007, now Pat. No. 8,672,905.

(51) Int. Cl.
*A61F 13/00* (2006.01)
*A61F 13/45* (2006.01)
(Continued)

(52) U.S. Cl.
CPC ........ *A61F 13/45* (2013.01); *A61F 13/00017* (2013.01); *A61F 13/00038* (2013.01); *A61F 13/00042* (2013.01); *A61F 13/00046* (2013.01); *A61F 13/00063* (2013.01); *A61F 13/538* (2013.01); *A61F 15/00* (2013.01); *A61F 13/069* (2013.01); *A61F 13/08* (2013.01); *A61F 2013/0054* (2013.01);
(Continued)

(58) Field of Classification Search
CPC .............. A61F 13/0206; A61F 13/0209; A61F 2013/00229
See application file for complete search history.

(56) References Cited

U.S. PATENT DOCUMENTS 3,364,931 A 1/1968 Hirsch .......................... 604/366
3,678,933 A 7/1972 Moore et al. .................. 604/366
(Continued)

FOREIGN PATENT DOCUMENTS

DE 2953373 1/1981 ............ A61M 35/00
DE 40 30 465 4/1992 ......... A61F 13/0203
(Continued)

OTHER PUBLICATIONS

Communication from EPO in corresponding foreign patent application, pp: 1-6 (dated Dec. 12, 2013).

*Primary Examiner* — Susan Su
(74) *Attorney, Agent, or Firm* — David G. Rosenbaum; J. Peter Paredes; Rosenbaum IP, P.C.

(57) ABSTRACT

The subject of the invention is a wound care article for extraction and control of wound fluids, comprising at least one first fluid-absorbing structure (1; 10; 36), which is surrounded by a liquid-permeable, first enclosure (2), and a liquid-permeable, second enclosure (3) comprising two enclosing surfaces (13.1, 13.2). The wound care article is thus characterized in that the first enclosure (2) is covered or supported on at least one of its flat sides (4.1, 4.2) by at least one fluid-absorbing material layer (6.1, 6.2; 6.3), which is arranged (FIG. 1*a*) between the first enclosure (2) and one of the enclosing surfaces (13.1, 13.2) of the second enclosure (3).

28 Claims, 14 Drawing Sheets

(51) Int. Cl.
*A61F 15/00* (2006.01)
*A61F 13/538* (2006.01)
*A61F 13/06* (2006.01)
*A61F 13/08* (2006.01)
*A61F 13/53* (2006.01)

(52) U.S. Cl.
CPC .............. *A61F 2013/0074* (2013.01); *A61F 2013/00136* (2013.01); *A61F 2013/00153* (2013.01); *A61F 2013/00157* (2013.01); *A61F 2013/00174* (2013.01); *A61F 2013/00229* (2013.01); *A61F 2013/00246* (2013.01); *A61F 2013/00519* (2013.01); *A61F 2013/00536* (2013.01); *A61F 2013/00617* (2013.01); *A61F 2013/00731* (2013.01); *A61F 2013/00748* (2013.01); *A61F 2013/00855* (2013.01); *A61F 2013/00914* (2013.01); *A61F 2013/00927* (2013.01); *A61F 2013/00936* (2013.01); *A61F 2013/4518* (2013.01); *A61F 2013/530802* (2013.01)

(56) References Cited

U.S. PATENT DOCUMENTS

| | | | |
|---|---|---|---|
| 3,871,376 A | 3/1975 | Kozak | 128/275.1 |
| 3,872,862 A | 3/1975 | Hume | 128/165 |
| 4,055,180 A | 10/1977 | Karami | 604/368 |
| 4,382,441 A | 5/1983 | Svedman | 604/291 |
| 4,537,184 A | 8/1985 | Williams, Jr. | 602/8 |
| 4,592,750 A | 6/1986 | Kay | 604/337 |
| 4,728,642 A | 3/1988 | Pawelchak et al. | 514/57 |
| 4,820,293 A | 4/1989 | Kamme | 604/368 |
| 4,969,880 A | 11/1990 | Zamierowski | 604/305 |
| 5,027,803 A | 7/1991 | Scholz et al. | 602/8 |
| 5,086,763 A | 2/1992 | Hathman | 602/42 |
| 5,171,208 A | 12/1992 | Edenbaum et al. | 602/6 |
| 5,171,302 A * | 12/1992 | Buell | A61F 13/47227 604/358 |
| 5,318,504 A | 6/1994 | Edenbaum et al. | 602/8 |
| 5,383,871 A | 1/1995 | Carlin et al. | 604/385 |
| 5,470,306 A | 11/1995 | Doubleday | 602/8 |
| 5,476,664 A | 12/1995 | Robinson et al. | 424/443 |
| 5,487,889 A | 1/1996 | Eckert et al. | 424/93.1 |
| 5,505,720 A * | 4/1996 | Walters | A61F 13/47236 604/358 |
| 5,520,621 A | 5/1996 | Edenbaum et al. | 602/8 |
| 5,540,922 A | 7/1996 | Fabo | 424/402 |
| 5,549,584 A | 8/1996 | Gross | 604/313 |
| 5,614,283 A * | 3/1997 | Potnis | A61F 13/5323 428/131 |
| 5,636,643 A | 6/1997 | Argenta et al. | 128/897 |
| 5,759,570 A | 6/1998 | Arnold | 424/443 |
| 5,885,237 A * | 3/1999 | Kadash | A61F 13/00042 424/445 |
| 6,071,267 A | 6/2000 | Zamierowski | 604/289 |
| 6,096,942 A * | 8/2000 | Hack | A61F 13/0203 602/41 |
| 6,140,257 A | 10/2000 | Kershaw et al. | 442/4 |
| 6,191,341 B1 | 2/2001 | Shippert | 604/383 |
| 6,333,093 B1 | 12/2001 | Burrell et al. | 428/194 |
| 6,398,767 B1 | 6/2002 | Fleischmann | 604/313 |
| 6,429,350 B1 * | 8/2002 | Tanzer | A61F 13/5323 604/367 |
| 6,441,268 B1 | 8/2002 | Edwardsson | 604/378 |
| 6,626,891 B2 | 9/2003 | Ohmstede | 604/543 |
| 6,685,681 B2 | 2/2004 | Lockwood et al. | 604/305 |
| 6,689,934 B2 | 2/2004 | Dodge, II et al. | 604/367 |
| 6,966,901 B2 | 11/2005 | Leisner et al. | 604/337 |
| 7,048,706 B2 | 5/2006 | Cea | 602/26 |
| 7,172,565 B2 | 2/2007 | Termanini | 602/8 |
| 7,381,859 B2 | 6/2008 | Hunt et al. | 602/46 |
| 7,524,315 B2 | 4/2009 | Blott et al. | 604/543 |
| 7,612,248 B2 | 11/2009 | Burton et al. | 602/58 |
| 7,951,100 B2 | 5/2011 | Hunt et al. | 602/2 |
| 8,187,210 B2 | 5/2012 | Hunt et al. | 602/2 |
| 2002/0038099 A1 | 3/2002 | Griffiths et al. | 602/54 |
| 2002/0065494 A1 | 5/2002 | Lockwood et al. | 604/313 |
| 2002/0069988 A1 | 6/2002 | Yahiaoui et al. | 162/123 |
| 2003/0045846 A1 * | 3/2003 | Sawyer | A61F 13/53 604/365 |
| 2003/0088229 A1 * | 5/2003 | Baker | A61F 13/53717 604/385.101 |
| 2003/0225383 A1 * | 12/2003 | Glaug | A61F 13/535 604/367 |
| 2004/0030304 A1 | 2/2004 | Hunt et al. | 604/317 |
| 2004/0054338 A1 | 3/2004 | Bybordi et al. | 604/313 |
| 2004/0249328 A1 | 12/2004 | Linnane et al. | 602/43 |
| 2005/0240220 A1 | 10/2005 | Zamierowski | 606/215 |
| 2006/0009744 A1 | 1/2006 | Erdman et al. | 604/385.01 |
| 2006/0147250 A1 | 7/2006 | Tereschouk | 401/133 |
| 2006/0240116 A1 | 10/2006 | Jolley | 424/535 |
| 2008/0004559 A1 | 1/2008 | Riesinger | 602/46 |
| 2008/0009812 A1 | 1/2008 | Riesinger | 604/305 |
| 2008/0119802 A1 | 5/2008 | Riesinger | 604/313 |
| 2008/0243044 A1 | 10/2008 | Hunt et al. | 602/58 |
| 2008/0312572 A1 * | 12/2008 | Riesinger | A61F 13/00008 602/43 |
| 2010/0305490 A1 | 12/2010 | Coulthard et al. | 602/43 |
| 2011/0213286 A1 * | 9/2011 | Riesinger | A61F 13/0203 602/43 |

FOREIGN PATENT DOCUMENTS

| | | | |
|---|---|---|---|
| DE | 3850798 | 7/1994 | A61B 19/00 |
| DE | 195 44 255 | 3/1997 | A61F 13/00 |
| DE | 19517699 | 11/1999 | A61B 17/03 |
| DE | 199 50 646 | 4/2001 | A61L 15/20 |
| DE | 100 59 439 | 8/2001 | A61F 5/44 |
| DE | 103 01 835 | 7/2004 | A61F 13/0203 |
| DE | 202004017052 | 6/2005 | A61M 1/08 |
| DE | 202004018245 | 7/2005 | A61M 27/00 |
| DE | 10059439 | 12/2005 | A61F 5/44 |
| DE | 103 61 306 | 10/2006 | A61L 15/44 |
| DE | 202006005966 | 10/2006 | A61F 13/15 |
| DE | 102007019622 | 10/2008 | A61F 13/02 |
| DE | 102007030931 | 1/2009 | A61P 17/02 |
| EP | 0 762 860 | 12/1997 | A61F 13/02 |
| EP | 1 129 734 | 9/2001 | A61M 1/00 |
| EP | 1 177 781 | 2/2002 | A61F 5/441 |
| EP | 1 640 023 | 3/2006 | A61L 15/00 |
| EP | 1 942 851 | 7/2008 | A61F 13/00 |
| EP | 1 985 270 | 10/2008 | A61F 13/02 |
| GB | 692578 | 6/1953 | |
| GB | 2272645 | 5/1994 | A61L 15/42 |
| WO | WO 1983/02054 | 6/1983 | A61F 13/18 |
| WO | WO 1996/05873 | 2/1996 | A61M 1/00 |
| WO | WO 1999/01173 | 1/1999 | A61M 27/00 |
| WO | WO 2001/10363 | 2/2001 | A61F 5/445 |
| WO | WO 2001/24754 | 4/2001 | A61F 13/472 |
| WO | WO 2001/89431 | 11/2001 | A61F 5/00 |
| WO | WO 2003/094813 | 11/2003 | A61F 13/02 |
| WO | WO 2004/014444 | 2/2004 | A61L 15/34 |
| WO | WO 2004/098476 | 11/2004 | A61F 13/15 |
| WO | WO 2005/123170 | 12/2005 | A61M 27/00 |
| WO | WO 2006/048240 | 5/2006 | A61F 13/00 |
| WO | WO 2006/048246 | 5/2006 | A61F 13/00 |
| WO | WO 2006/056294 | 6/2006 | A61M 1/00 |

* cited by examiner

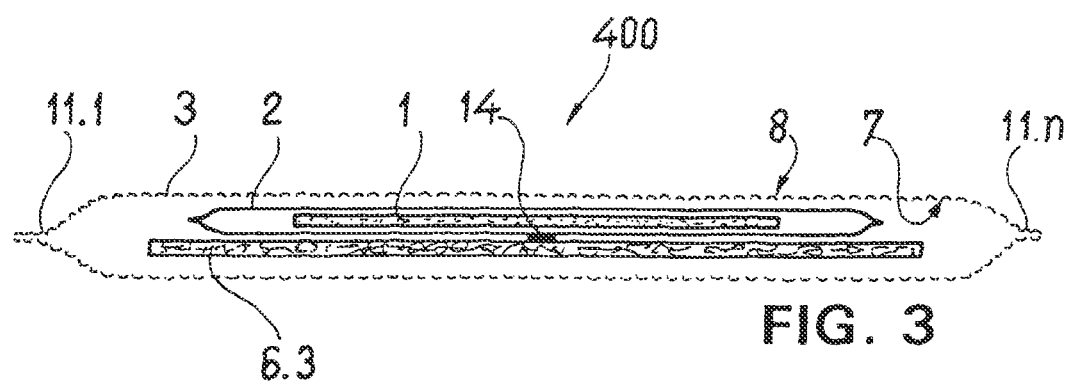
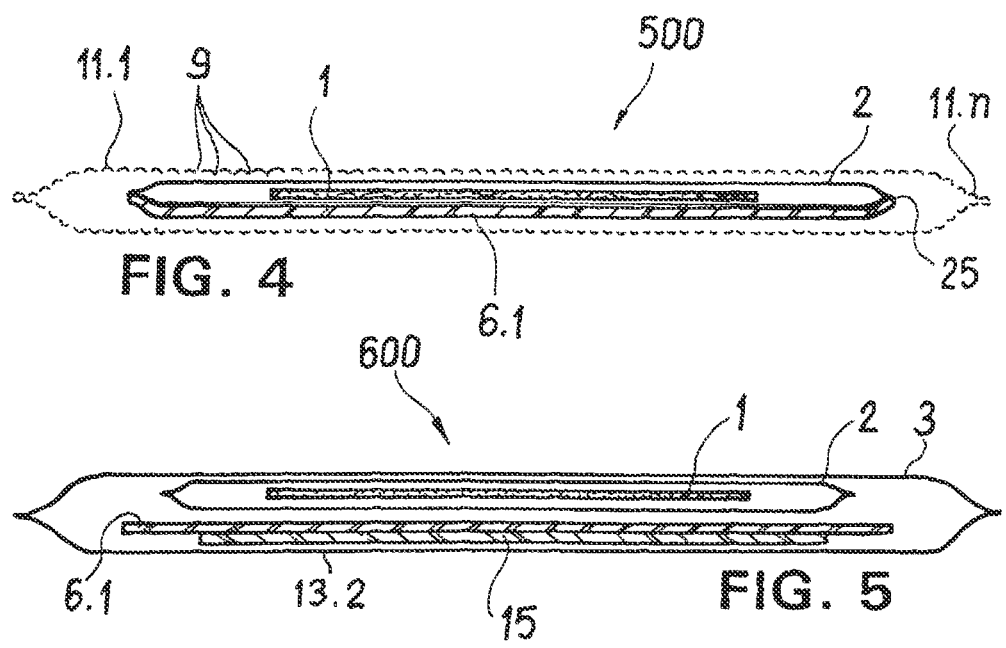
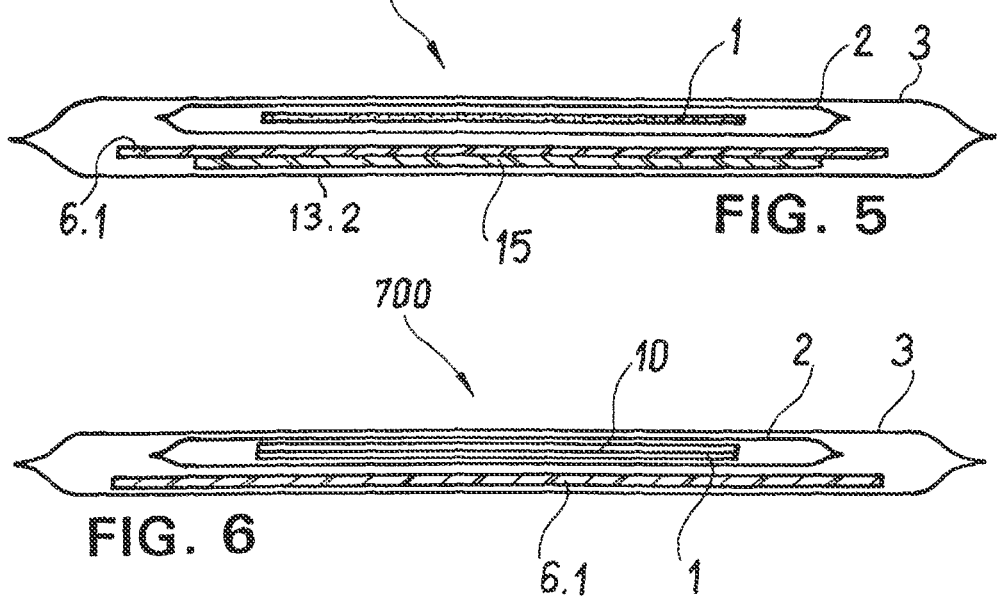

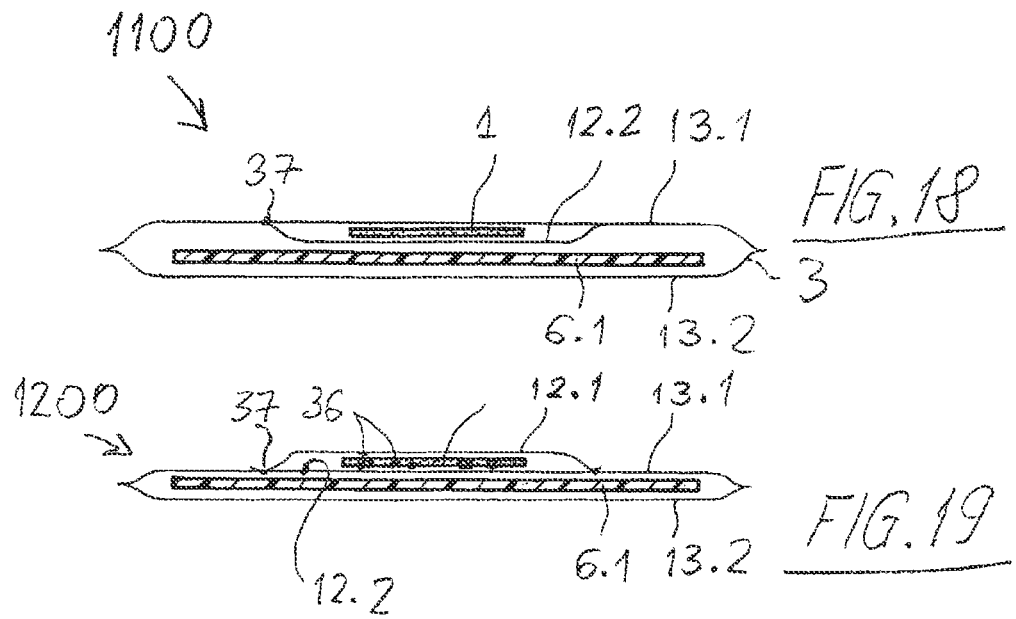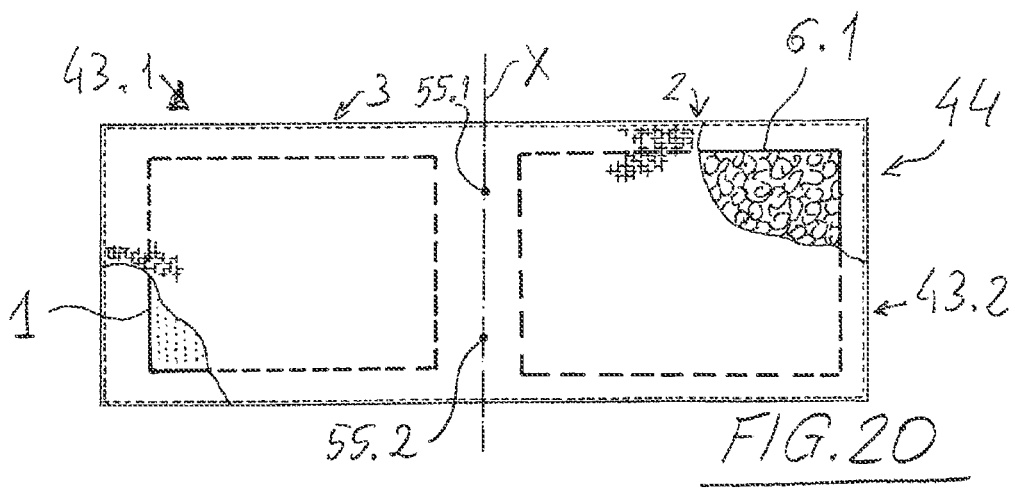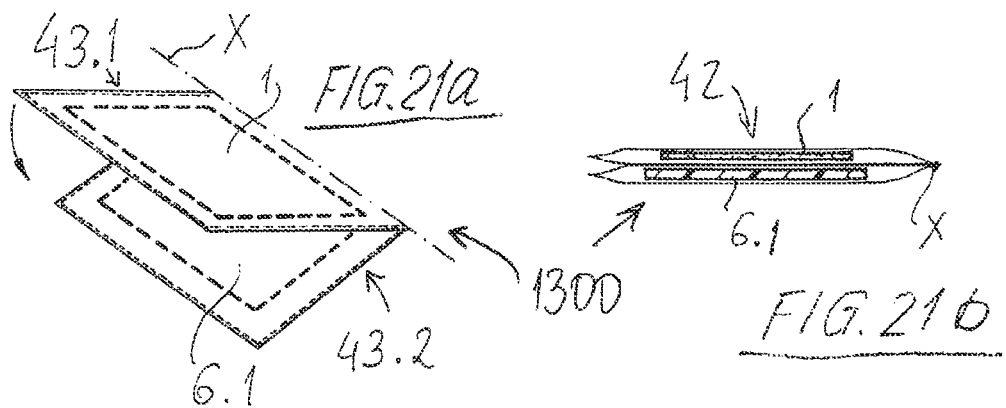

WOUND CARE ARTICLE FOR EXTRACTION AND CONTROL OF WOUND FLUIDS

CROSS-REFERENCE TO RELATED APPLICATIONS

The present application is a continuation of U.S. Ser. No. 12/443,989, filed Jun. 21, 2010, which claims priority to PCT Application No. PCT/EP07/60304, filed Sep. 28, 2007, which claims priority to German Application No. 10 2006 047 041.9, filed Oct. 2, 2006, all of which are incorporated herein in their entireties.

BACKGROUND OF THE INVENTION

The invention concerns a pillow-shaped wound care article for the extraction and control of wound fluids as described and claimed herein.

This type of wound care article is especially suitable for the extraction of exudate from chronic wounds, such as (for example) when diabetes, ulcus cruris, and similar illnesses occur.

The term "exudate" designates a wound fluid that is secreted from the blood plasma through the inflammatory processes of the wound oedema. Just as the blood is responsible for the transportation of nutrients and other substances and thus for supplying various parts of the body, the exudate serves in a very similar way to supply the wound bed and the healing processes occurring therein. To perform adequately in these various functions, it contains a broad spectrum of components, resulting in a specific density slightly greater than that of water. This distinguishes it from "transsudate", which is derived from non-inflammatory processes, and which has a significantly lower specific density with a lesser cell and protein content. In addition to providing nutrients for the fibroblasts and epithelial cells, the exudate coordinates the various processes of local and chronological wound healing, by means of its high concentration of growth factors and cytokines. These are formed primarily by thrombocytes, keratinocytes, macrophages, and fibroblasts. They influence the motility, migration, and proliferation of the various cells involved with healing the wound. Thus the migration of cells into the wound base is promoted, as well as the supply for the newly created granulation tissue through angiogenesis. Wound cleansing is also promoted by the exudate. It contains various serin, cystein, and aspartate proteases, as well as matrix-metalloproteases, which by their strictly regulated activity remove irreversibly damaged tissue, and thus prepare the wound bed for subsequent phases of healing.

Particular components of the physiological exudate are salts, glucose, cytokine and growth factors, plasma proteins, proteases (especially matrix-metalloproteases), granulocytes, and macrophages.

If a significant progression corresponding to the various phases of the wound healing process does not occur within a few weeks, it is called a chronic wound. However, an exudative phase lasting even as long as three days is regarded as a complication, and may be referred to as a pathologic exudation, which may contribute to a chronic character of the wound. The fundamental underlying causes are usually complex and may indeed be of systemic nature. In view of the previously mentioned importance of the exudate for wound healing, it is not surprising, that complications in healing of the wound will be reflected in significantly altered composition and the effects of the exudate.

The exudate, which normally promotes healing, will lose its positive effect for chronic wounds through (among other things) a shift in concentration of the individual components of the exudate. In particular, the concentration of inflammatory cytokines and proteases is significant increased in pathological exudates. Whereas, the concentration of growth factors is reduced. A particularly important difference results in respect to the activity of the matrix-metalloproteases mentioned earlier. In addition to preparing the wound bed, they also take part later in rebuilding the granulation tissue to scar tissue. These enzymes are normally formed as inactive pre-enzymes, and their activity is regulated through corresponding inhibitors (tissue inhibitors of metalloproteases: TIMP's), which even have a simultaneous positive effect for cell growth. In chronic exudate the activity of the proteases seems to be increased because of disturbances in this regulating system, which may contribute to an active regression of the wound. With regard to the concentration of its components, pathological exudate has gotten out of the balance required for a progressive healing of the wound. The leads to various complications, which contribute further to the deterioration and chronic character of the wound.

A wound care article of the type mentioned above serves especially to absorb this mentioned chronic exudate, and thus to promote healing of the wound. The applicant is aware of such a wound care article from Patent DE 100 59 439. In the case of this familiar wound care article, the wound care article's additional, internal enclosure made of cotton has the function to inhibit direct contact between the mucous cells of the patient's wound or body cavity and the absorbent pad. The effect of the wound care article applied on the patient's wound or body cavity—especially the absorptive force acting on the wound—is the same, no matter whether its "left" or "right" side is used.

SUMMARY OF THE INVENTION

The purpose of the invention is to provide an appropriate wound care article, which permits greater flexibility in wound treatment for the caretakers. An additional purpose is to make available an appropriate wound care article, which gives the caretakers the opportunity to react differently, corresponding to the requirements of the wound to be treated. A further purpose to make available an appropriate wound care article, which is suitable on one side for application to weak to moderately exuding wounds, and with the other side rather to strong exuding or secreting wounds.

These purposes are solved by a wound care article with the characteristics of the primary claim presented. The sub-claims designate preferred construction forms. It must be noted that the area terms are always to be understood as including the respective limiting values.

Hereafter a wound care article is envisioned, in which the first enclosure is covered or supported on at least one of its flat surfaces by at least one fluid-absorbing material layer, which is arranged between the first enclosure and one of the enclosing surfaces of the second enclosure.

The first enclosure can be surrounds by the second enclosure. In this respect it is preferably envisioned that the first fluid-absorbing structure is surrounded by a likewise liquid-permeable internal enclosure consisting of two enclosing sheets. In this "enclosure in enclosure" construction form the fluid-absorbing material layer is thus surrounded only by the second, external enclosure, whereas the first fluid-absorbing structure is surrounded by the external and the first, i.e. internal enclosure.

In what follows, the term "wound care article" shall designate in particular a wound covering, preferably a flat wound covering or a wound care cloth. Said wound covering may be designed to be both absorbing as well as non-absorbing or only insignificantly absorbing. In particular, the term "wound care article" may also be understood as a collection of various products, which are arranged in a specified position on the wound to be treated. This collection may form a physical unit, in that the various products are collected in a common enclosure, or—possibly without an enclosure—connected adhesively to one another. However, the collection may also be present in form of a "kit", in which the various products are arranged with the aid of a compress in the specified arrangement on the wound to be treated.

In a different construction form, the first enclosure and the second enclosure with the therein applied first structure and the material layer may form bandage booklet, in which both enclosures are foldable on at least one fold line or at least one long or spotted seam. The first enclosure merges preferably as a single piece of material into the second enclosure.

The fluid-absorbing material layer is preferably a foam material pad, which may also contain cellulose fibres or particles. The material layer may contain hydraulic fibres and/or alginates. However, the material layer may also be made from other materials, as long as they have the ability to absorb liquids.

The foam material mentioned is preferably polyurethane, for example, "cross-linked" foams.

In particular it is provided that the first fluid-absorbing structure comprises a greater absorptive capacity and a higher extractive ability than the second fluid-absorbing structure, i.e. the aforementioned material layer.

The term "pillow-shaped" should be understood in the following to be a substantially flat structure, which primary consists of two side walls that form the exterior enclosure, whereby the side walls are connected at their edges by adhesive, pressure, welded, or thermal connections, forming seams or borders. Since the exterior enclosure surrounds a fluid-absorbing material layer (or pad), this configuration results in a flattened pillow form, which with increasing fluid absorption continually achieved a more strongly curved cross section, especially on that side of the wound care article on which the fluid-absorbing structure is located.

The term "extraction and control of wound fluids" should be understood in the following to mean that the wound care article according to this invention actively extracts and retains wound fluids. These wound fluids are especially known pathologic exudates, which in principle may be emitted for as long as 48 to 72 hours. Moreover, this term implies that both absorbing structures are intended for use as wound care articles.

The first fluid-absorbing structure and the material layer may be equal in surface area, but preferably the structure of the wound care article is such that the first fluid-absorbing structure is smaller in surface area than the material layer. This results in various possibilities for construction:
  The enclosing surface of the second enclosure may simultaneously form an enclosing surface of the first enclosure, whereby the enclosing surface of the first enclosure can be attached to the enclosing surface of the second enclosure by an encircling seam;
  The first enclosure, composed of two enclosing sheets, may be connected to the enclosing sheet of the second enclosure by an encircling seam, whereby in both cases is the condition applies that the first enclosure is smaller in surface area than the second enclosure.

Furthermore, for the bandage booklet described above, the first fluid-absorbing structure can likewise be smaller in surface area than the material layer.

The first fluid-absorbing structure is preferably a fleece-like pad. This may contain cellulose, especially carboxymethylcellulose, or alginate. The pad may also be woven in form.

Alginates are obtained from brown algae and are woven to form a fibrous fleece. Chemically these are polysaccharides, in fact calcium and/or sodium salts of alginic acids. Alginates can bind up to 20 times their own weight of liquid, whereby the wound exudate is stored in the empty spaces. The $Ca^{2+}$ ions contained in the alginate lattice are exchanged for the $Na^+$ ions in the exudate, until the saturation level for Na-ions in the alginate is reached. The wound care article thereby swells up and the alginate fibres are turned into a gelatinous structure by the swelling of the fibres.

Carboxymethylcellulose is particularly present in form of sodium carboxymethylcellulose, and is marketed under the name of "Hydrofaser", among others. In hygienic and wound products the fibres are delivered into a flat matrix. Through the extraction of liquid from the wound exudate, the fibres are gradually converted into a gelatinous pillow, which holds the liquid and does not release it again. For this the fibres are so structured, so that the wound exudate is extracted only vertically. This means that, as long as the capacity is sufficient, the exudate will not flow past the edge of the wound. By this method a maceration of the wound edge can be effectively prevented.

The pad-like absorbing structures manufactured in particular from sodium carboxymethylcellulose are very similar in their material properties, their methods of functioning, as well as in their indicative spectrums to the alginate products. They are likewise applied in dry condition on the wound, absorb wound exudate relatively strongly and quickly, and are converted thereby into a translucent, cloudy gel. The capacity for absorbing secretions is high, and (this) takes place in a vertical direction. Thus the desired gel develops only in the region of the moist wound surface. The wound edge and the area surrounding the wound remain dry, no maceration develops.

The first fluid-absorbing and/or the material layer comprises preferably of at least one super-absorbent substance. These are preferably Super-Absorbing Polymers (SAP), which may be arranged in a matrix containing cellulose fibres. These preferably used super-absorbents are one reason that the first fluid-absorbing structure comprises a greater extractive capacity and/or absorptive strength than a sodium carboxymethylcellulose, alginate, or foam pad.

Super-absorbing polymers (SAP) are plastics, which are able to absorb many times their own weight—up to 1000 times—in liquid. Chemically, these are a copolymer of acrylic acid (propenoic acid, $C_3H_4O_2$) and sodium acrylate (sodium salt of acrylic acid, $NaC_3H_3O_2$), whereby the relative ratios of the two monomers may vary. In addition, a so-called core connecter (Core-Cross-Linker, CXL) is added to the monomer solution, which links the long-chain polymer molecules with chemical bridges at various places to each other ("networking" them). Because of these bridges the polymer become insoluble in water. When water or aqueous salt solutions intrude in the polymer particles, they swell up and tighten this network at the molecular level, so that the water no longer can escape without help.

The super-absorbent polymers may be present in the wound care article according to the invention in the form of a granulate, a powder, a casting, a pressing, and/or a foam.

The super-absorbent particles may be present in powder or granulate form in a particle size between from 100 μm to about 1000 μm. The weight ratio between the super-absorbents and the fluid-absorbing structure lies in the region from 0.01 to about 0.5.

The cellulose-containing pad forming the first fluid-absorbing structure may be of "airlaid" type.

Furthermore, it is possible to manufacture the first fluid-absorbing structure in the form of a casting, a pressing, and/or in the form of shavings. The casting or the pressing may consist of either many shavings manufactured from the padding, i.e. cuttings, or exclusively of powder, granulate, or thread-shaped super-absorbent particles. The shavings themselves may also be loaded with super-absorbent particles.

The fluid-absorbing material layer may be arranged loose in of the second enclosure, or may be attached to the enclosure. The connection may be implemented by means of glue, welding, and/or by means of applied pressure, they may be constructed over an area, or also in spot or in line form.

All pharmaceutically acceptable adhesives may be considered for the adhesive. In particular, polysaccharide-containing adhesives (such as starch glue, for example), protein-containing adhesives, or acrylate glue, such as also find use as tissue glue, may be considered. Furthermore as the inventor has established, gels, or W/O (water in oil), or O/W (oil in water) emulsions may be used, to bind both pads adhesively to one another (i.e. adhesively in the above senses). The welding may be implemented for example through use of heat and/or ultrasound, if needed in combination with pressure.

However, a construction of the wound care article is preferred, in which both the second fluid-absorbing material layer, and also the first internal enclosure, as well as the first fluid-absorbing structure present in the internal enclosure are freely movable.

In this arrangement the wound care article comprises two different sides with differing levels of absorbing performance Depending on the level of exudation, the caretakers can decide which side of the wound care article should be applied to the wound. For strongly exuding wounds, it is preferable to apply the side on which the first fluid-absorbing structure with super-absorbent particles to the wound, whereas for weakly exuding wounds the side applied to the wound is that on which the aforementioned material layer is arranged, such as foam material or just a pad comprising sodium carboxymethylcellulose. Should the exudation of the wound in the latter case increase in the course of treatment, exudate from wound flows out of the reverse-side of the cellulose pad or out of the foam material and will be reliably extracted and bound there by the strongly absorbent first fluid-absorbing structure with super-absorbent particles.

In addition to its high extractive capacity for exudates, a wound care article constructed in this manner has the property that it:
a) extracts and retains necrotic particles, pathogens, and especially germs,
b) extracts and retains exudates, but does not extract mucous, and
c) results in a high atmospheric humidity due to the relatively high vapour pressure, which contributes to the generation of a moist environment that promotes wound healing.

The use of foam material or a hydro-fibre pad contributes to the protection of the edge of the wound. Besides avoiding maceration, the padding effect of the foam material is achieved. A desirable constant temperature within the wound area can be sustained over an extended time period, because the wound care article is relatively thick, and ensures improved thermal insulation.

However, it can also be provided that the material layer (the second fluid-absorbing pad) is also provided with super-absorbent particles, to increase its fluid absorption capacity.

The alginates mentioned are polysaccharides composed of 1,4 linked α-L-guluronate and β-D-mannuronate. Alginates form homopolymeric areas, in which mannuronate or guluronate is present in (so-called) blocks. These blocks are called G or M blocks. In the region of the G-blocks and M-blocks a type of folder structure develops, which plays a substantial role in gelling. In particular the G-blocks form a regular zigzag structure.

In the form of fibrous calcium or calcium/sodium alginates, they are familiarly used as wound compresses or as wound tampons. Alginates have a large absorptive capacity and build a viscous gel that is stabile in form, by extraction of wound secretions and micro-organisms with strong swelling that keeps the wound moist (fluid absorption up to 20 times of their own weight). In addition, alginates act haemeostatically because of the release of calcium ions.

The first fluid-absorbing structure may also be supported by a pad containing alginate, which likewise may also be arranged within the internal enclosure. In this construction form the pad containing alginate is preferably on the reverse-side of the parallel-aligned second material layer. Should the extractive capacity of the alginate pad be insufficient, the pad-like fluid-absorbing structure will take up the extra wound exudate.

The second fluid-absorbing material layer may also be joined over its surface to a pad containing alginate, which may lie between the second fluid-absorbing material layer (pad) and the enclosing surface of the external, second enclosure.

The presence of the pad containing alginate on the side reversed from the first structure may be seen as advantageous by technical personnel, since it allows multiple selection possibilities for the use of an absorbing structure with predetermined absorption capacity for a certain wound type and estimated exudate amount. In this case it is advantageous, that the pad containing alginate has a smaller surface than the second fluid-absorbing material layer has, because an effective protection for the wound edge must be considered.

The fluid-absorbing material layer may be perforated. This consists preferably of relatively large holes of possibly varying geometry. Round pores with a diameter of 2 mm to 15 mm may be provided. Furthermore, the perforated material layer may lie on an additional, preferably perforation-free fluid-absorbing pad, preferably consisting of sodium carboxymethylcellulose or foam material.

The coarse particles of the wound exudate may attach to the pores. The remaining thin liquid wound exudate reaches through the open-celled, hydrophilic foam structure into its depth. It may also be advantageous that the perforated foam pad directed toward the enclosing surface has larger pores than the other covering pad. In addition, it is also conceivable to use a so-called integral skin foam-as wound covering, which comprises of only a single foam layer, with a pore density that continuously recedes, in this case beginning from the side near the wound, in the direction of the wound covering.

The internal and/or exterior enclosures are comprised preferably of hydrophobic material, for example, of polypropylene, or from a hydrophobically treated natural material, such as cotton.

The hydrophobic characteristics of the enclosure (especially the external enclosure) prevent adhering to the wound surface and in addition help the wound exudate particles to reach the inside of the enclosure more quickly.

Both enclosures may be manufactured from other plastic sheets, especially a polyurethane or polyethylene foil, or from artificial spider web sheeting.

The material of the internal and/or external enclosures may be structured in such a manner that the enclosure comprises a rough interior surface and a smooth exterior surface. The rough interior surface of the enclosure is preferably formed by funnel-shaped perforations, each of which narrows in the direction of the interior surface, and end in a freely opening edge ("open collar"). This rough interior surface acts against shifts of the contents in the enclosure, so that an attachment with glue points is not necessary. Accordingly, the smooth exterior surface of the enclosing material may be formed by curved material sections, extending between the perforations. Such an enclosing material may be called "three-dimensional", in contrast to one that is flat on both sides.

The exterior enclosure is preferably manufactured of such "three-dimensional" material, whereas the internal is preferably manufactured from a "two-dimensional" material, i.e. a material that is flat on both sides. The adjective "flat" is understood here to be a structure of the enclosing material, in which the perforations and the material sections lying in between comprises no elevations. To increase the friction between both enclosures still more, the material of the internal enclosure may be rough. The perforations on both enclosures may be different. In particular, the perforations of the external enclosure may be larger than those of the internal enclosure, so that the thick (viscous) wound exudate and/or small cellular remains may travel into the inside of the external enclosure. Whereas the thin liquid wound exudate comes through the internal enclosure, which can finally be taken up by the first pad.

However, construction of the internal and external enclosures both with smooth or rough surfaces is also possible.

The wound care article according to the invention may be applied loosely on the wound or body cavity, and affixed over its entire surface to the patient's body with a secondary bandage or a covering sheet. Accordingly, the wound care article may be part of an occlusive or semi-occlusive system, or also a part of a compression or reduced pressure system.

The wound care article may be provided with its own attachment means, for example, in that the enclosing surfaces of the external enclosure are in each case provided with a peripheral adhesive strip on both of its flat sides. The doubled adhesive strips make it possible to attach the wound care article with the flat side selected by the technical personnel to the patient's body. It is understood that medically harmless substances come into question as adhesives, in particular ones already approved, for example, those based on polysaccharides. To facilitate the handling of the wound care article provided with peripheral adhesive strips, it is envisioned to provide in each case both of the opposing adhesive strips with a removable, for example, silicone-type protective strip.

The material layer of the described wound care article may comprise of at least one central, window-like opening, in which an alginate insert fits, in particular calcium alginate, o also a bag with granulate or thread-shaped superabsorbent particles.

Because of the danger of maceration, pads of certain alginates may not reach beyond the wound edge. This requirement is countered by a structured framing of the alginate, which may consist both of sodium carboxymethylcellulose or also of foam material. The alginate insert can have direct contact with the respective wound, in that a window is provided in the enclosing surface of the external enclosure.

Metal ions, especially zinc, manganese, calcium, or silver ions may be added to the components of the wound care article, especially to the pad, to support the local wound healing processes. Furthermore, honey and its derivatives, enzymes, saponins, especially those of vegetable derivation (these are contained, for example, in Ribwort Plantain (*Plantago lanceolata*), or other disinfecting substances as well as vitamins, such as vitamin A, $B_9$, $B_{12}$, C, and E may be employed. Preferred are especially such components that have radical-capturing or antioxidant characteristics.

The foam material-pad may be open or closed-pore, hydrophilic or hydrophobic. If a closed-pore foam material is employed, it is recommended to introduce continuous openings and/or holes in the foam material.

Additional advantages are achievable in combination with a foam construction within a common further, external enclosure. Two forms of wound relief are achieved:

For strong exudation, the side of the wound care article is applied to the wound, on which the first fluid-absorbing pad shows toward the surface of the external enclosure, and by means of the desired strong absorption effect, the wound care article relieves the wounded area, in that it extracts the undesirable pathologic exudate, which comprises harmful hormonal and component materials. Interstitial, intercellular, as well as cellular and also vascular spaces achieve close to a physiological irrigation, so that perfusion, arterial influx, venous recovery, and trans-membranous diffusion are optimized, and not by means of long diffusion paths which are interfered with by pathologic aqueous solutions and reactive bio-relevant enzymes. For cell growth requires the arterial influx of proteins, oxygen, as well as the contributions from vessels, nerves, and functional supports of the immune defence.

In contrast with this realization, the existing therapeutic practice employs the application of bandages with comparatively low absorptive strength and unsatisfactory retention. Often foam bandages are used, which under pressure release what little water has been extracted, along with components that interfere with wound healing. The focus thus drifts to surface of the wound and is occupied with treating resulting effects and control of superficial cosmetic aspects.

It may thus be recommended to use foam material pad as the full-surface primary contact layer, as long as the advantages of the pad interspersed with super-absorbent particles find additional use. This may be achieved in that the foam has contact with the wound and the specified pad is applied directly on its reverse, first to ensure the equalization to a very non-homogenous wound base morphology by means of a foam, which as flow-through and contact structure transfers the wound fluids directly to the pad. It is also conceivable to fulfil this function by means of alginates, carbon bandages, or cotton and fleece materials.

For weaker exudation, the foam side can be applied to the wound. Here the wound care article achieves an indirect factor for wound relief, in that it uses its absorptive strength to dry the back side of the foam. For this it is necessary that the foam is nearly soaked, so that the current flow through the foam is achieved through (for example) capillary effects, and develops as a gentle inflow into the fluid-absorbing pad. Here the wound care article dries the back of the foam and forms a secondary reservoir, which adds the capacity of the pad to the capacity of the foam, even though it does not have significant contact with the wound.

The wound care article according to the invention can be called a multiple-phase bandage, in particular a multiple-phase primary bandage, which permits an improved control of exuded wound fluid. The wound exudate flows into the foam and is "cached" there. The superfluous wound exudate is then absorbed by the internal absorbing structure, which consists of the pad containing cellulose and the internal enclosure.

When foams are used in the wound bandages, these tend to roll up at their edges. The use of a "internal" absorbing structure formed by the pad and the internal enclosure on the reverse creates a desirable mechanical counter-force here, and contributes to retaining full-surfaced contact with the wound area.

The principle of the individual wound care article according to the invention makes it possible to carry out a simplified visual check of the emitted wound exudate with the use of absorbing structures interspersed with super-absorbent particles, provided that the absorbing structure is employed in the form of set sizes adjusted corresponding to the wound.

A great advantage is that the absorbed wound exudate can take and remain at a set position in the wound care article, so that the surrounding skin near the wound is not attacked by the wound exudate.

The wound care article according to the invention may be provided with a stretchable covering sheet, which prevents the respective maximum volume increase of the wound care article during of the absorption process only minimally or not at all. Such a covering sheet may for example be laid wrinkled and/or pleated and/or folded and/or bellows-shaped. For this the existing application refers to the Applicant's Patent DE102007019622, whose published content should be fully included here. In particular, a wrinkled covering sheet may prove to be advantageous, since it is elastic in all directions. Should the folded or wrinkled covering sheet extend past the periphery of the wound care article, it is recommended to thermally smoothen the surface extending beyond the wound care article.

The wound care article according to the invention can satisfy a wound-filling function, if the alginate or foam-like material layer is given a spiral form with the assistance of a punching tool or another thermal and/or mechanical process. The alginate or foam-like material layer mentioned may also comprise multiple, concentrically applied round or rectangular frames.

Preferably the frames are connected and arranged stepwise with one another by means of bridges consisting of the same material, so that the material layer punched to form multiple frames does not disintegrate when unfolded.

In both cases, when applied to the wound the punched material layer may protrude at least partially as a "wick" from the second enclosure's enclosing surface toward the wound, when corresponding crossing cuts are worked into enclosing surface. The cuts should be implemented in such a manner, that the wick unfolding into the wound is not impeded by the rectangular or triangular enclosing surface sections that develop. It is recommended accordingly to place the cuts diagonally or radially on the enclosing surface towards the wound. When used, the wick imposes pressure in the enclosing surface, whereby the enclosing surface sections are shifted from their flat position, permitting the extension of the wick. The first structure lying over of the wick supports the absorption process.

As already mentioned, at least one of the enclosing surfaces of the second enclosure forms a common enclosing surface with a corresponding enclosing surface of the first enclosure. This construction is particularly advantageous for a substantially smaller enclosing surface of the first enclosure, which is connected by means of an encircling seam with the enclosing surface of the second enclosure. Thus in a top view of the enclosing surface of the second enclosure, two encircling, concentrically applied seams are present. For the swollen wound care article, the inner seam pulls together and prevents a spreading of the first structure, especially when a strong welling out is experienced by the first absorbent structure. Such a construction of the wound care article is especially suitable for deep wounds.

The construction principle described also covers two full enclosures, of which the first enclosure comprising two enclosing surfaces is attached to the second enclosure comprising two enclosing surfaces by means of an encircling seam, whereby the first enclosure is smaller than the second.

Preferably it is envisioned that in addition, the wound care article comprises at least one nutritious, at least one disinfecting or decontaminating, and/or at least one protease-limiting active substance and/or compound of active substances.

The active substance and/or compound of active substances acting as a disinfectant may be (for example) a composition of at least one vitamin or vitamin derivative, a metal ion, as well as a detergent. It may also be a BUS (bacteriocin-like inhibitory substance) or a coated magnetic particle.

The active substance and/or compound of active substances working nutritiously may be a composition containing at least the components of an enteralen and/or parenteralen dietary substance. It may also be at least one effective element selected from the group comprising insulin, recombinant insulin, proinsulin, an insulin-like growth factor (IGF), an insulin replacement and/or a diabetic-specific, non-glucose and non-saccharose-based energy source.

The active substance and/or compound of active substances affecting protease limitation may be at least one effective element selected from the group comprising protease limiters, super-absorbent polymers, chelating agents for divalent cations, collagens, coated magnetic particles, acids, buffers, non-pathogenic acid-producing micro-organisms, probiotics, and/or symbiotics.

Further connections and background about the nutritious, disinfecting or decontaminating, and/or protease-limiting active substances and/or substance compositions are described in the Applicant's Patent DE102007030931 for the present application, whose contents are referenced fully here. The Patent DE102007030931 describes additional nutritive, disinfecting or decontaminating, and/or protease-limiting active substances and/or compounds of active substances, which likewise should be treated as published for this application.

Furthermore, the wound care article according to the invention may also be employed in a wound maintenance system for wound drainage with use of reduced pressure. Such systems are for example made known to the Applicant of the present invention in the Patents DE202004017052, WO2006048246, and DE202004018245, whose published content should be regarded as belonging to the present invention.

The first (Patent) mentioned makes known a means for wound treatment by use of reduced pressure, comprising a gas-tight wound covering element, which when applied to the patient's body forms an empty space between the respective wound and the wound covering element, and at least one connection element, which stands in contact with the space, and by means of which the air present in the space may be evacuated, whereby the wound covering element is underlaid by at least one wound care article that absorbs the wound secretions, whose volume increases in the course of the absorption process, so that the absorbed wound secretions remain within the wound care article and thus underneath the wound covering element until the wound care article is removed from the body of the patient, the wound care article comprises at least one layer of a textile section enriched with super-absorbent substances, which is surrounded by a liquid-permeable enclosure, and the layer has a surface area in top view of its flat side that is 3% to 90% smaller than that of the enclosure, so that when the wound care article is near its entire filling capacity, it can approach a circular cross section.

The second (Patent) mentioned makes known a multiple-component bandage for wound treatment of human or animal bodies by use of reduced pressure, comprising: a wound covering element for mounting on skin and mucous tissue surfaces, at least one connection point, which stands in contact with the wound area, and by means of which the materials present in the wound area can be evacuated, whereby this comprises super-absorbent polymers, by means of which the absorbed wound secretions remain bound to polymers in the wound area until these are removed from the wound area, whereby the polymers support reciprocal synergies with the sub-atmospheric pressure through their absorptive capacity.

The last (Patent) mentioned makes known a means of drainage for wound treatment by use of reduced pressure, comprising a gas-tight wound covering element composed of foil-like material, which when applied to the patient's body forms is fastened adhesively to the skin surface around the wound area, and which forms a sealed space remaining between respective wound and the wound covering element, and at least one drainage tube, which can be placed into the space, by means of which materials present in the space can be evacuated, and at least one wound care article applied within the space that absorbs the wound secretions, which comprises at least one layer of a textile section enriched with super-absorbent substance(s), which is surrounded by a liquid-permeable enclosure, so that the absorbed wound secretions remain within the wound care article and thus underneath the wound covering element until the wound care article is removed from the body of the patient, and in which the wound covering element comprises a gas-tight, sealable opening for handling, through which the wound care article may be laid in the space and removed from the space.

Moreover, the wound care article according to the invention may comprises a form adjusted to anatomic conditions. For this it may, for example, be constructed in form of a sleeve, which can be slipped over an arm or a leg or a joint, or in form of a bandage adapted to the heel, elbow joint, etc.

The wound care article according to the invention may in addition be so constructed, that it is suitable for placement around a surgically implanted tube. For this, the wound care article may comprise for example at least one opening, which makes it possible to place the bandage around a cable on the body of a patient (for example a drainage tube or a catheter), whereby wound care article is associated with a second, likewise surface-area wound care article, which lies at a distance from the first wound care article, whereby the distance is bridged by a connective strip or link. The Applicant of the present invention is familiar with such a wound care article, for example from Patent DE202006005966, whose contents should be appended to the published content of the present description to their full extent.

In this connection it is also preferably envisioned, that the wound care article comprises at least one agent that can limit bleeding or the susceptibility to bleeding.

The agent mentioned may be at least one chemically and/or physiologically affecting active substance, or a compound of active substances, or at least one physically affecting effective element. The Applicant of the present invention is familiar with such a wound care article, for example from the Patent DE102007036755.

For this, the wound care article for example may be:

i) constructed as a substantially flat material section comprising absorbing material, composed of an absorbent fleece with super-absorbent polymers, as well as at least one chemically and/or physiologically affecting active substance or a compound of active substances distributed therein, ii) a pressure or compression bandage, or in combination with either, iii) a combination of a primary, non-absorbing or only insignificantly absorbing wound covering, comprising at least one chemically and/or physiologically affecting active substance or a compound of active substances, and a secondary wound covering applied peripherally to this primary wound covering, which contains super-absorbent polymers, whereby a diffusion barrier may be arranged between both, iv) in the form of a bandage package, comprising a primary wound covering with at least one chemically and/or physiologically affecting active substance or a compound of active substances, as well as a wrapping section applied to the wound care article, which comprises super-absorbent polymers at least in sections, and/or (v) a material section with long extent comprising absorbing material, whereby the material section comprises elastically deformable characteristics, and whereby the material section comprises super-absorbent polymers as well as perhaps at least one chemically and/or physiologically affecting active substance or a compound of active substances.

The chemically and/or physiologically affecting active substance or compound of active substances is preferably at least one material or a composition that comprises anti-haemorrhagic characteristics. These materials are known by the general term "haemostatics".

The chemically and/or physiologically affecting active substance or compound of active substances is preferably at least one material or a composition that comprises anti-haemorrhagic characteristics. These materials are known by the general term "haemostatics". The term "chemically and/or physiologically affecting active substance or a compound of active substances" should be understood in this context as such active substances or compounds of active substances, which are capable of limit bleeding or the susceptibility to bleeding, without requiring physical force to be used. The action path here is a chemical and/or physiological interaction with the wound environment.

The physically affecting acting element is for example a binding, a pressure pad, a pressure bandage, or a compression bandage. The term "physically affecting acting element" should thus be understood in this context to be an effective element, which is capable of limiting the bleeding or susceptibility to bleeding by physical means, i.e. by the action of pressure, suction, cooling, and other similar things.

The term "compound of active substances" should be understood in the following not just as a compound in the chemical sense, but rather in particular a composition of active substances that synergistically produce an effect.

The active substances or compounds of active substances mentioned may be present as instant granules or powder.

Some example configurations of the wound care article according to the invention are listed in the following table yet again:

| | First absorbent structure | (Second) absorbent pad | Enclosure configuration | Illustration |
|---|---|---|---|---|
| 1 | "airlaid" pad with super-absorbents, circular | PU-foam materialor CMC with or without super-absorbents, rectangular | enclosure in enclosure peripheral connection | (FIG. 9) |
| 2 | "airlaid" pad in form of shavings with super-absorbents | PU-foam material or CMC with or without super-absorbents | enclosure in enclosure or enclosure over enclosure | FIG. 22 FIG. 17 |
| 3 | "airlaid" pad with super-absorbents | PU-foam material with perforations | enclosure in enclosure | FIG. 2 |
| 4 | "airlaid" pad with super-absorbents | CMC with window, and an alginate insert there | enclosure in enclosure | FIG. 12, FIG. 13 |
| 5 | "airlaid" pad with super-absorbents | PU-foam material (perhaps as shavings) or CMC | enclosure over enclosure | FIG. 17a |
| 6 | "airlaid" or alginate pad with or without super-absorbents | PU-foam material or CMC with or without super-absorbents | bandage booklet | FIG. 20, FIG. 21 |
| 7 | "airlaid" or alginate pad with or without super-absorbents | PU-foam material punched (spiral or block form) | enclosure in enclosure or enclosure over enclosure or bandage booklet | FIG. 25, FIG. 26, FIG. 28 |
| 8 | alginate pad with or without super-absorbents | or CMC in cascading form (pyramid-shaped) | enclosure in enclosure | FIG. 27b |

It is to be understood that in the scope of the present invention many further combinations are possible.

BRIEF DESCRIPTION OF THE FIGURES

The present invention will be described more precisely through showing and discussing the following figures and examples. It should be considered that the figures and examples merely have a descriptive character and are not intended to limit the invention in any way. The construction examples are described in detail by these figures. The figures show:

FIG. 3 A third construction form of the wound care article, with a structural external enclosure;

FIG. 4 A fourth construction form of the wound care article, with a structural external enclosure and a foam material-pad applied peripherally to the internal enclosure;

FIG. 5 A fifth construction form of the wound care article, with an alginate layer laminated on the foam material;

FIG. 6 A sixth construction form of the wound care article, with a doubled pad within the first internal enclosure;

FIG. 18 A twelfth construction form of the wound care article, represented as in the cutaway according to FIG. 17*a*;

FIG. 19 A thirteenth construction form of the wound care article, likewise represented as in the cutaway according to FIG. 17a;

FIG. 20A fourteenth construction form of the wound care article, here in opened form, in a top view of its flat side;

FIG. 21a The wound care article according to FIG. 20 during as it is folded together; in a perspective view;

FIG. 21b The wound care article folded together according to FIG. 21a, in a schematic side view;

DETAILED DESCRIPTION OF THE PREFERRED EMBODIMENTS

Figure 1A:
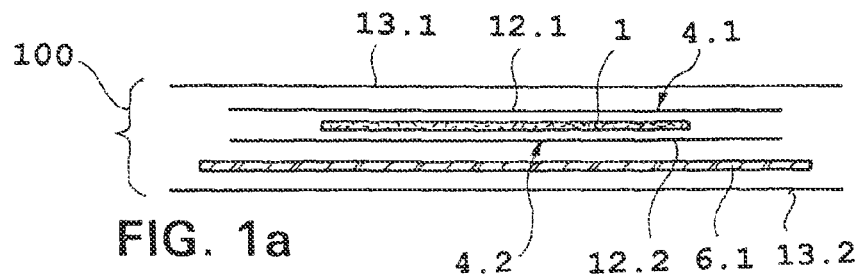
FIG. 1*a* A wound care article according to the invention in its first construction form, before sealing the enclosing surfaces, in a schematic exploded view.

In FIG. 1a a first wound care article is represented designated with indicator 100, consisting of two external enclosing surfaces 13.1, 13.2, two internal enclosing surfaces 12.1, 12.2 and a first fluid-absorbing structure 1 positioned between the internal enclosing surfaces 12.1, 12.2. The said structure 1 exists in form of a cellulose-containing, fleece-like pad. The enclosing surface 12.1 is directed with its first flat side 4.1 towards the exterior enclosing surface 13.1 and with its second flat side 4.2 towards a foam-like material layer 6.1 that lies between the internal enclosing surface 12.2 and the external enclosing surface 13.2.

Figure 1B:
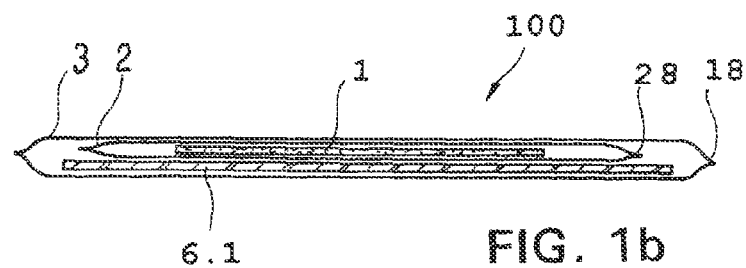
FIG. 1*b* The wound care article according to FIG. 1*a*, ready for use, in a cutaway view perpendicular to the flat side of the wound care article.
Figure 7:
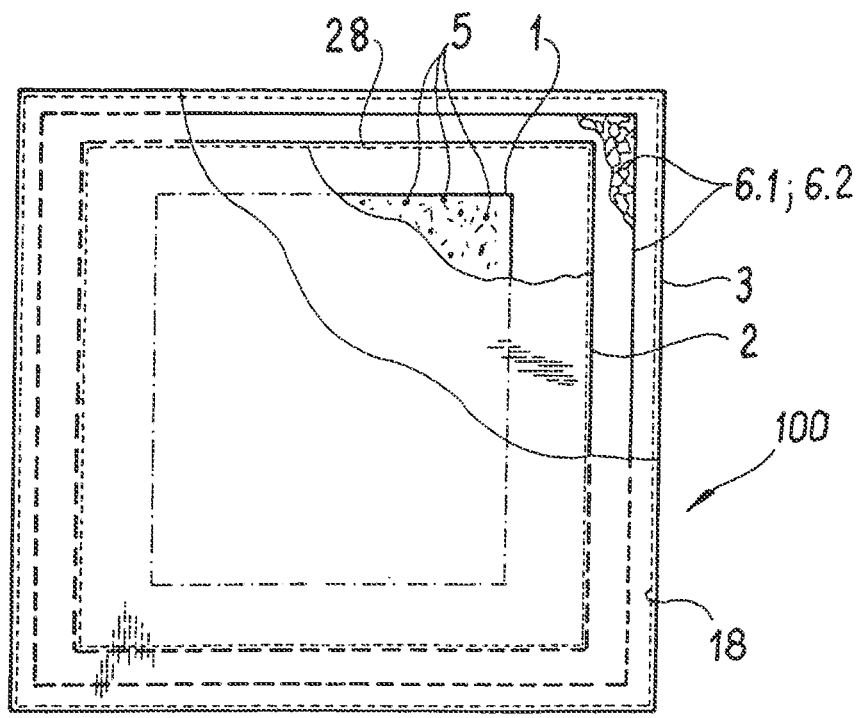
FIG. 7 The wound care article according to FIG. 1*b*, in a top view of its flat side.
Figure 8:
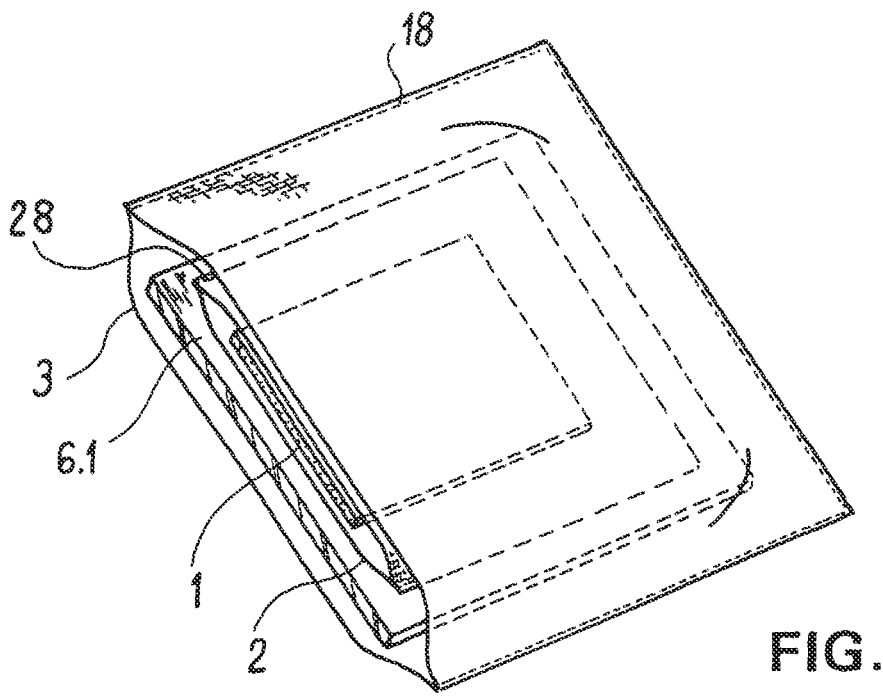
FIG. 8 A section of the wound care article according to FIG. 1*b*, in a perspective view.

As especially shown in FIGS. 1b, 7 and 8, the enclosing surfaces 12.1, 12.2 surrounding the structure 1 as well as the external enclosing surfaces 13.1, 13.2 are each sealed with one another by a peripheral ultrasonic seam 28; 18 with a first internal and, correspondingly, a second external enclosure 2; 3, so that the pad-like structure 1 is completely surrounded by the internal enclosure 2 and, correspondingly, the internal enclosure 2 as well as the foam-like material layer 6.1 by the external enclosure 3. All enclosing surfaces 12.1, 12.2; 13.1, 13.2 of the wound care article 100 are permeable to fluid. As material for the manufacture of the enclosing surfaces 12.1, 12.2; 13.1, 13.2 a perforated polyurethane foil is used.

For the manufacture of the material layer 6.1 in the existing case open-celled polyurethane soft foam in a thickness between 2 mm and 3 mm is considered. The total thickness of the manufactured new wound care article 100 is about 5 to 6 mm. Both enclosures 2; 3 as well as the material layer 6.1 are not connected with one another. The pad-like structure 1 lying within the internal enclosure 2 is arranged freely movable in enclosure 2. The pad-like structure 1 contains a quantity of granular and powdery super-absorbent particles 5 (cf. FIG. 7).

Optionally, the second fluid-absorbing pad on the internal enclosure 2 can be fixed by an adhesive point 14. FIG. 3 shows a wound care article 400, where the enclosing surface 12.2 of the internal enclosure 2 is connected with the material layer 6.3 made of sodium carboxymethylcellulose by means of the centrally applied adhesive point 14. As sodium carboxymethylcellulose layer, for example, the material known under the trade name "HYDROFASER" is used (owner: E.R. Squibb & Sons, L.L.C., Princeton, N.J., USA). The surface area of the material layer 6.3 existing of sodium carboxymethylcellulose is larger than the internal enclosure 2. The exterior enclosure 3 even is made of a hydrophobic material, here: polyurethane foil manufactured comprising funnel-shaped perforations 9 and curved material sections 11.1, . . . 11.n, extending between the perforations 9, resulting in a rough interior surface 7 on one side and in a smooth, wound-protective exterior surface 8 on the other side.

A wound care article 500 represented in FIG. 4 shows an exterior enclosure 3 identical to the construction form according to FIG. 3. The exterior enclosure 3 surrounds likewise the foam-like material layer 6.1 and the internal enclosure 2 including the flat structure 1, however, the internal enclosure 2 and the foam-like material layer 6.1 are peripherally connected with one another by a welded seam 25.

The FIG. 5 shows a further wound care article (fifth construction form, reference symbol 600), that is a further development of the first wound care article 100 represented in FIGS. 1a, 1b. Between the material layer 6.1, hereafter called foam material-pad, and the enclosing surface 13.2 of the external enclosure 3 an alginate layer 15 is arranged with a somewhat smaller surface area than the foam material-pad 6.1. Alternatively, both layers 6.1 and 15 can have the same surface. The alginate layer 15 is laminated on the foam material-pad 6.1 in the known manner.

A further development of the first wound care article 100 represented in FIGS. 1a, 1b is also shown in FIG. 6. In this case two pads are shown, evenly lying in the internal enclosure 2, one of those represents the fluid-absorbing structure 1 directed towards the material layer 6.1. A further pad 10 made of calcium alginate is laminated on the structure 1, both having the same surface area. The alginate-containing pad 10 is on the reverse-side of the foam material-pad 6.1.

Figure 2:
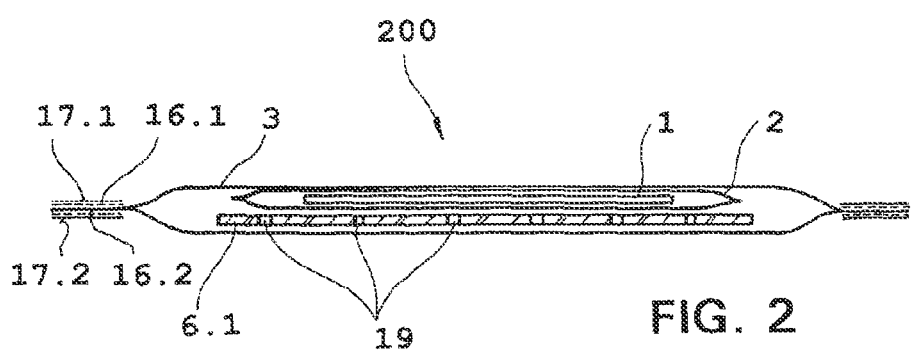
FIG. 2 A second construction form of the wound care article, with means of attachment, likewise in a cutaway view perpendicular to the flat side of the wound care article.

The FIG. 2 represents likewise a further development of the first wound care article 100 represented in FIGS. 1a, 1b. A wound care article designated with reference symbol 200 is provided with fixation means permitting to fix the wound care article on the patient's body. For this purpose, both enclosing surfaces 13.1, 13.2 of the external enclosure 3 are provided in each case on their external surfaces with a peripheral adhesive strip 16.1, 16.2 as well as with a removable, protective strip 17.1, 17.2 made of silicone paper. The foam material-pad 6.1 is provided with multiple end-to-end openings 19 (holes) in a diameter of about 4 mm. The advantage is that the two-sided provision of the fixation means allows fixing the wound care article with any random flat side on the patient's body.

Figure 14:
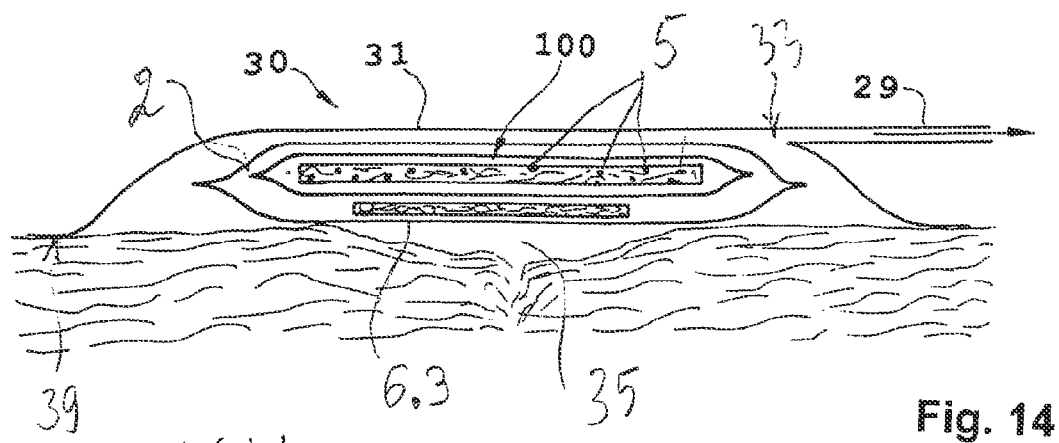
FIG. 14 Use of the wound care article according to FIG. 1 in a reduced-pressure system, in a schematic view.
Figure 15:
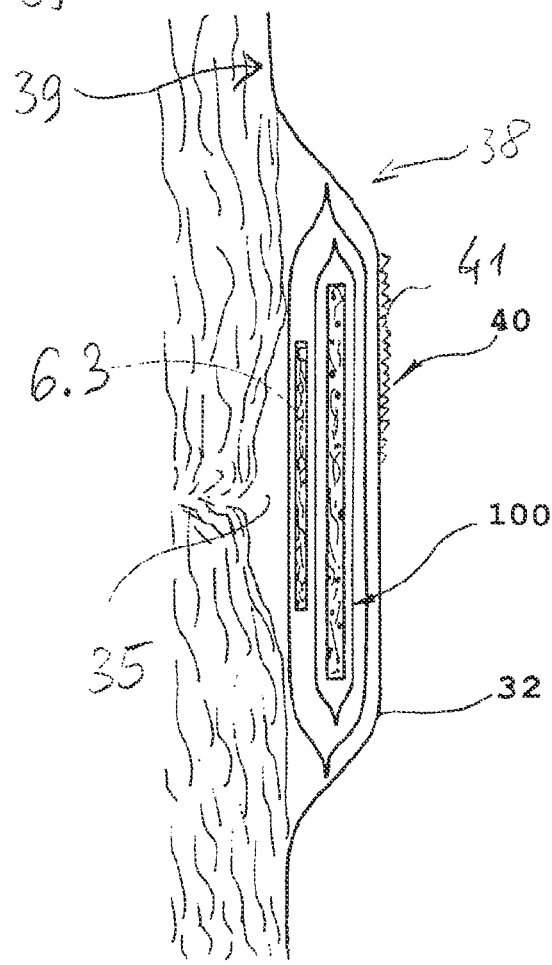
FIG. 15 Use of the wound care article according to FIG. 1 in an occlusive system, likewise in a schematic view.

The FIGS. 14 and 15 show schematically a use of the wound care article 100 in a reduced pressure system 30 and, correspondingly, in an occlusive system 40. The reduced pressure system 30 contains a covering sheet 31 impermeable to fluid and water vapour and a vacuum channel 29 following the covering sheet 31 through a schematically shown opening 33, being preferably positioned in parallel to the wound care article 100. The wound care article 100 comprises again an alginate-containing material layer 6.3 directed towards the wound 35, with a smaller surface area than the pad-like structure 1 lying within the internal enclosure 2. The fluid-absorbing structure 1 consists of fleece-like applied cellulose fibres and super-absorbent particles 5 distributed therein. The covering sheet 31 is not connected with the enclosing surface of the external enclosure 3.

The occlusive system 40 contains a liquid-tight, but water vapour permeable covering sheet 32 and the said wound care article 100, likewise comprising the alginate-containing material layer 6.3 directed towards the wound 35, having a smaller surface area than the structure 1 lying within the internal enclosure 2.

Both flexible covering sheets 31, 32 protrude the periphery 38 of the wound care article and are each provided with a peripheral adhesive surface 39 so that they can be fixed without any problems on the skin around the wound.

The covering sheet 32 shown in FIG. 15 is pleated (folded) so that its overall surface area is larger compared to a smooth sheet. This is advantageous and allows a wide extension of the covering sheet 32 during of the process of absorbing so that a considerable increase in volume of the wound care article will not lead to substantial counteracting forces caused by the covering sheet. The indicator 41 designates the schematic pleats in the covering sheet 32. In a not represented sample of construction the covering sheet is not pleated, but wrinkled. The crêpe-like covering sheet can extend in all directions.

Figure 9:
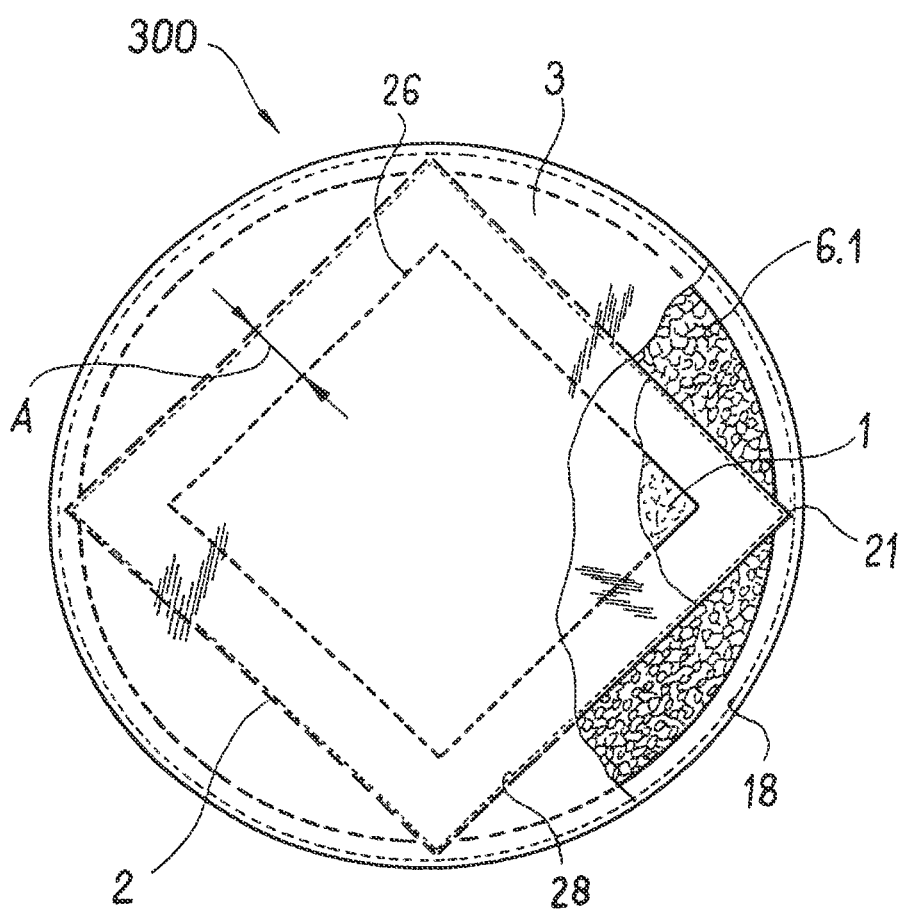
FIG. 9 A seventh construction form of the wound care article, in a top view of its flat side.

A round wound care article 300 is shown in FIG. 9. However, only the exterior enclosure 3 and the foam material-pad 6.1 are round, on the other hand the internal enclosure 2 as well as the pad-like structure 1 are square in the top view to the flat side of the wound care article 300, whereby the extents of the internal enclosure 2 are adapted to the interior of the external enclosure 3 in such a way that the internal enclosure 2 with all its four corners 21 is almost reaching the ultrasonic seam 18. This method excludes the undesirable shifts of the internal enclosure within of the external enclosure by simple means, without the use of adhesive (possibly not desired for medical reasons). Such a configuration can be realized very easily. As shown in FIG. 9, the pad-like structure 1 is smaller in surface area than internal enclosure 2 so that unfolding within enclosure 2 is fully possible during absorption. A distance designated with reference symbol A between the ultrasonic seam 18 of the internal enclosure 2 and an exterior edge 26 of the structure 1 can be variable at the periphery, when the stated extents of the structure 1 and the internal enclosure 2 will be kept.

Figure 10:
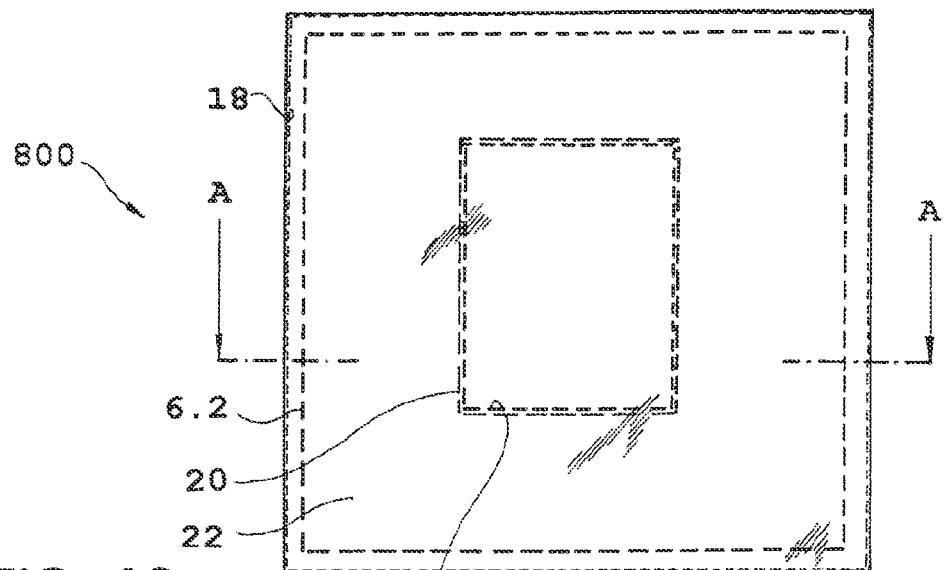
FIG. 10 An eighth construction form of the wound care article, with a centrally applied alginate insert, in a top view of its flat side.
Figure 11:
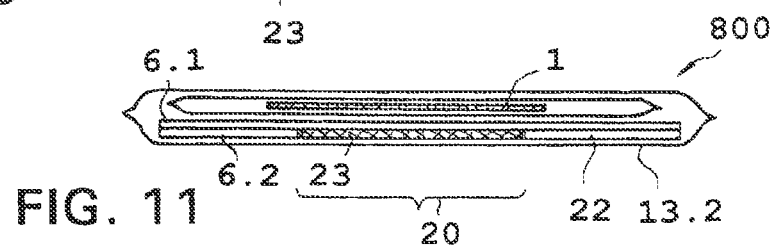
FIG. 11 A cutaway view A-A according to FIG. 10.
Figure 12:
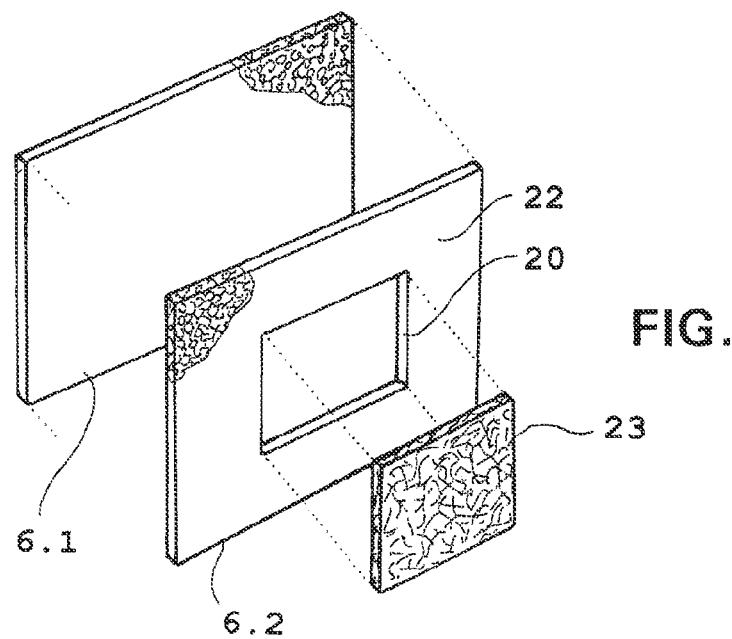
FIG. 12 An arrangement of two foam material-pads and the alginate insert in an exploded perspective view.

The FIGS. 10 and 11 represent a wound care article 800 consisting of the internal enclosure 2 with therein included fleece-like structure 1, of the external enclosure 3 and two superimposed foam material-pads 6.1, 6.2, whereby a rectangular, centrally applied opening 20 is punched out of the foam material-pad 6.2 directed towards enclosing surface 13.2 so that a framing 22 (cf. in particular FIG. 12) for an alginate insert 23 being positioned in the opening 20 is obtained.

Figure 13:
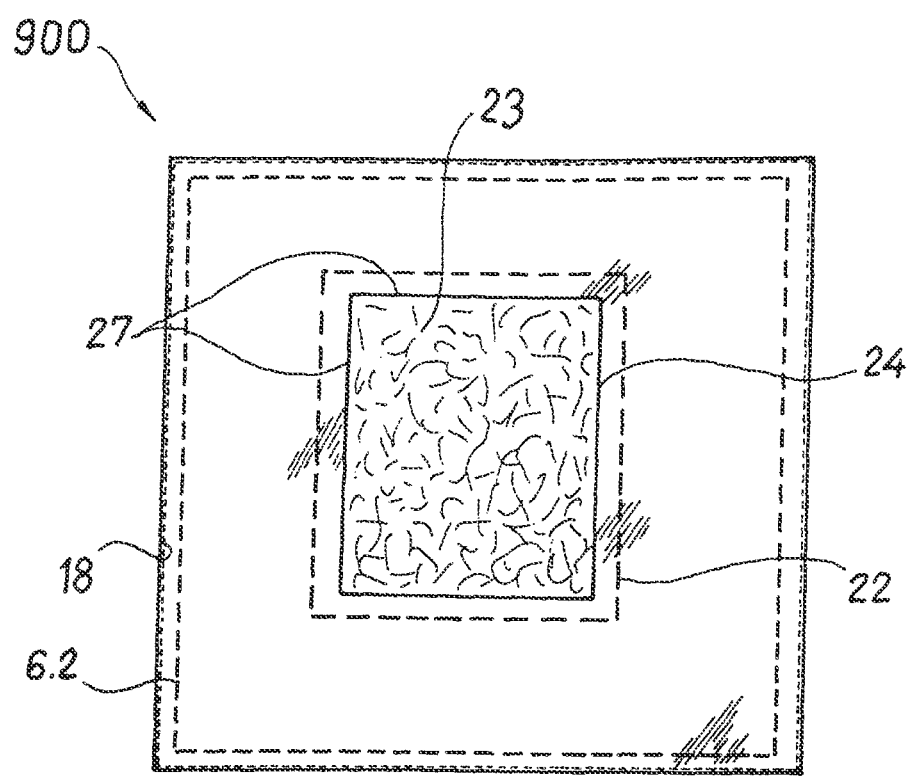
FIG. 13 A ninth construction form of the wound care article, with an alginate insert and a window, likewise in a top view of the flat side of the wound care article.

The FIG. 13 shows a similar wound care article 900, where a window 24 is punched out of the enclosing surface 13.2 of the external enclosure 3, whose edges 27 slightly overlap the alginate-containing insert 23. By this way, sufficient support for the insert 23 is ensured within the opening 22. The alginate-containing insert 23 can come into direct contact with the respective wound. Optionally, super-absorbent substance in form of powder, granulate or fibres can be inserted in the alginate-containing insert 23.

Figure 16:
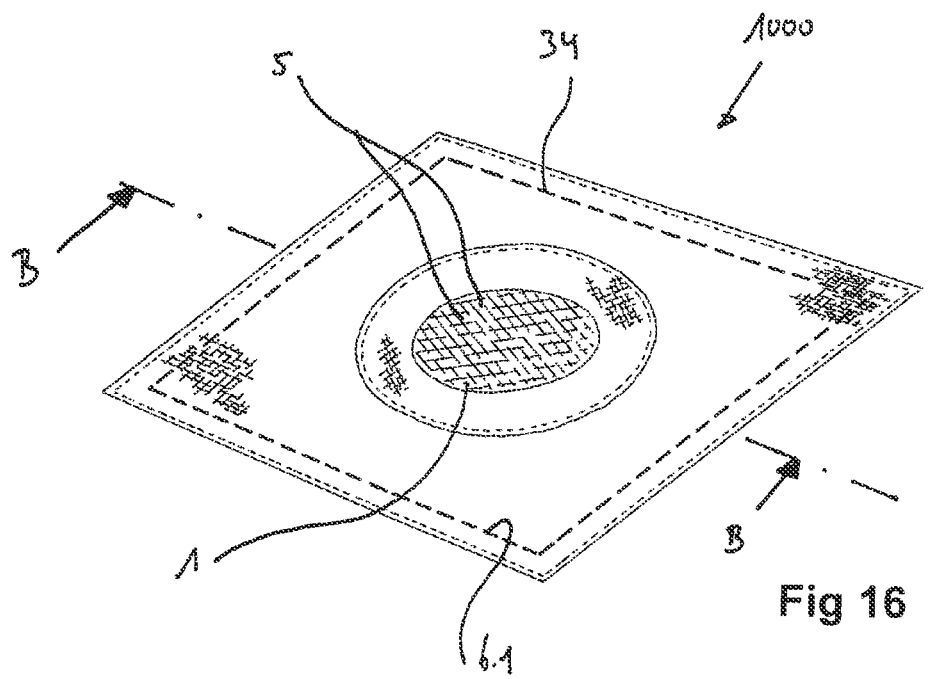
FIG. 16 An eleventh construction form of the wound care article, in a perspective view.
Figure 17:
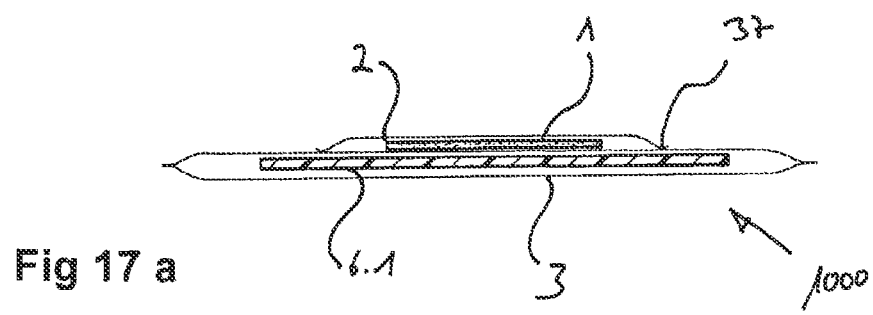
FIG. 17*a* A cutaway view B-B according to FIG. 16.
FIG. 17*b* The swollen wound care article according to FIG. 16, likewise in a cutaway view.
Figure 17:
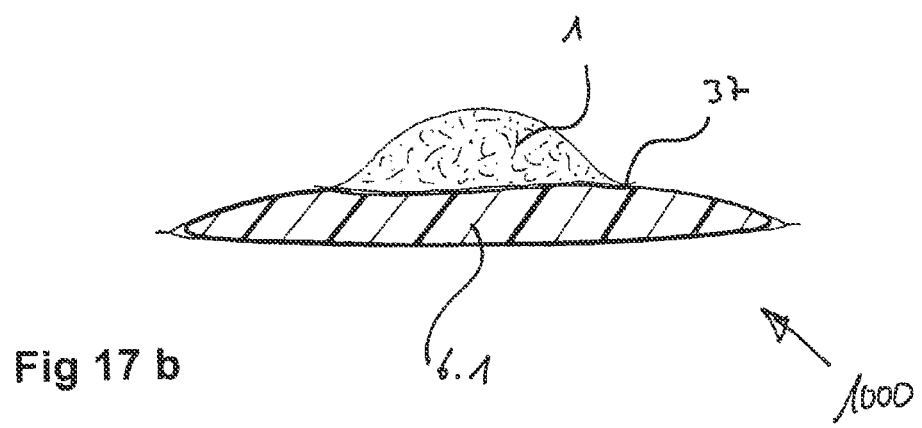

The FIGS. 16, 17a and 17b show a wound care article 1000, where the substantially smaller enclosing surface 12.1 of the first enclosure 2 is connected with the enclosing surface 13.1 of the second enclosure 3 by a circulating ultrasonic seam 37. This is done without a second enclosing surface 12.2 of the first enclosure 2. The smaller enclosure 2 with a round outline 34 is arranged centrally on the second enclosure 3. Within the second enclosure 3 the foam-like (polyurethane foam) material layer 6.1 and, correspondingly, within the first enclosure 2, a cellulose-containing pad (structure 1) is arranged moveably. The larger, in the present case square enclosure 3 has dimensions of 10×10 cm, and the smaller has a diameter of about 6 cm, in each case measured up to the corresponding ultrasonic seam. Based upon these dimensions of both enclosures 2; 3, the material layer 6.1 amounts to about 6.5 cm×6.5 cm, and the pad-like structure 1, however, has a diameter of about 4 cm.

The wound care article 1000 after an absorption process represented in FIG. 17b shows a moderately swollen foam material-pad 6.1 and a strongly swollen, almost hemispheric structure 1. This configuration of the swollen wound care article with a one-sided convex surface can adjust to the surface properties of a deep wound, fill it up, and thus accelerate the healing process. Moreover, due to the convex surface a permanent contact between absorbing materials and the wound base is ensured, thus assuring a permanent exudate uptake. These advantages are also valid for all other arrangements having a convex surface and/or permitting a wound filling.

Instead of structure 1 made of a cellulose-containing pad with super-absorbent particles 5 distributed therein, other highly absorbing materials, such as an alginate-pad, a casting of shavings and/or of super-absorbent particles can be used. FIG. 19 shows a wound care article 1200, whose structure is very similar to that of the wound care article 1000, whereby the smaller enclosure 2 contains a casting of shavings 36. The shavings 36 of average sizes from 3 mm to 5 mm are automatically cut out of a cellulose-like, multi-layered airlaid pad, fortified with super-absorbent particles. Tests have shown that a casting of shavings 36 having the same weight than an entire pad can absorb the same amount of fluid about 15% faster. The reason might probably be the increased surface of the shavings' construction form in comparison to an airlaid-pad of the same weight.

A particular advantage is that the shavings 36 can also be made out of the waste products from pad production.

This construction also offers the advantage that in contrast to a flat pad—the shavings can extend three dimensionally when swelling, thus forming a convex surface, similar to a casting, and, for example, can fill up wound cavities.

This characteristic reveals a healing accelerating effect. Due to the wound cavity filling, a permanent contact between absorbing materials and the wound base is ensured, which guarantees a permanent exudate uptake. These advantages are also valid for all other arrangements having a convex surface and/or permitting a wound filling.

In a further construction sample (not represented), likewise referring to the wound care article 1000, the smaller enclosure 2 has its both enclosing surfaces 12.1, 12.2. Therefore, the entire smaller enclosure 2 is applied to the second larger enclosure 3 and peripherally connected with the latter.

The FIG. 18 shows a wound care article 1100, whereby the first smaller enclosure 2 with its enclosing surface 12.2 directed towards material layer 6.1 is applied to enclosing surface 13.1 directed to the reverse side of the material layer of the second enclosure 3 by means of a peripheral ultrasonic seam 37. The function of the second, not existing enclosing surface 12.1 of the first enclosure 2 is taken over by the enclosing surface 13.1 of the second larger enclosure 3. Apart from that, the wound care article 1100 consists of the same parts mentioned in the description of the wound care article 1000 (FIGS. 16, 17a and 17b).

One of the wound care article 1300 represented in the FIGS. 20, 21a and 21b is a bandage booklet 42 (cf. FIG. 21a), resulting from folding up two wings 43.1, 43.2 of a common double covering 44 along a fold line X. FIG. 20 shows that the folded-up double covering 44 consists of the first enclosure 2 and the second enclosure 3, whereby the first enclosure 2 passes as one piece of material into the second enclosure 3. The wings 43.1, 43.2 are each made up of enclosure 2 or 3 and the corresponding absorbent materials. In the existing construction sample the first enclosure 2 contains a highly absorbing textile material, in this case the already mentioned pad-like structure 1, and the second enclosure 3 the likewise described foam-like material layer 6.1. Two spot joints 55.1, 55.2 are positioned along the fold line X separating the two enclosures 2; 3 having the same surface area in such a way that the absorbent materials within the double covering 44 cannot be shifted over the fold line. The fold line X can be replaced by a not represented, continuous seam; however, it can also be perforated to allow a separation of both halves by tearing them apart.

Figure 22:
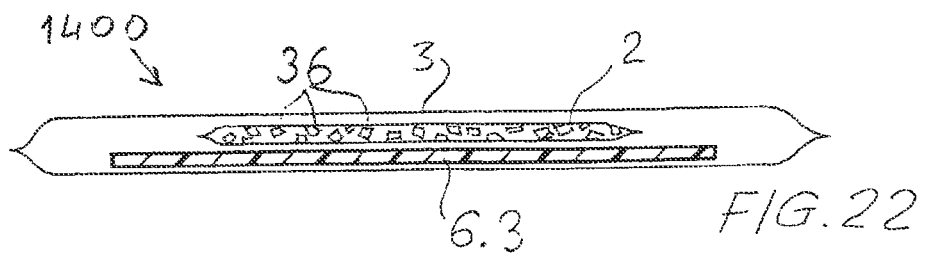
FIG. 22A fifteenth construction form of the wound care article, in a schematic side view.

A wound care article 1400 represented in FIG. 22 shows an "enclosure-in-enclosure"-configuration that is also shown in FIG. 1b, for example. The difference between both wound care articles 100 and 1400 is that the first internal enclosure 2 of the wound care article 1400 contains the already described shavings 36 cut out of the airlaid-pad and that the material layer 6.3 lying outside of the internal enclosure 2 consists of hydraulic fibres, i.e. of sodium carboxymethylcellulose, whereby the material layer 6.3 has a larger surface area than the internal enclosure 2.

Figure 23:
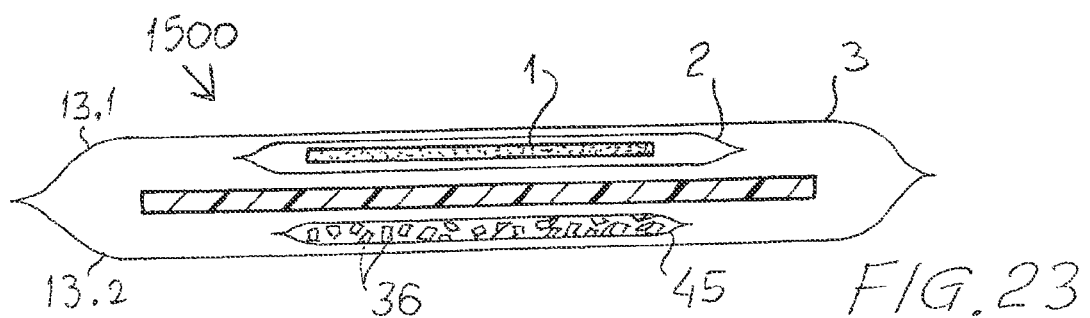
FIG. 23 A sixteenth construction form of the wound care article, with shavings in the internal enclosure, in a schematic side view.

The FIG. 23 shows again a wound care article 1500 consisting of the foam-like material layer 6.1 in the second external enclosure 3, the fluid-absorbing pad-like structure 1 in the first internal enclosure 2, and a casting of shavings 36, which are arranged in an additional internal enclosure 45 directed to the reverse-side of enclosure 2. Both internal enclosures 2, 45 are thus lying each between the material layer 6.1 and an enclosing surface 13.1, 13.2 of the external enclosure 3.

Figure 24:
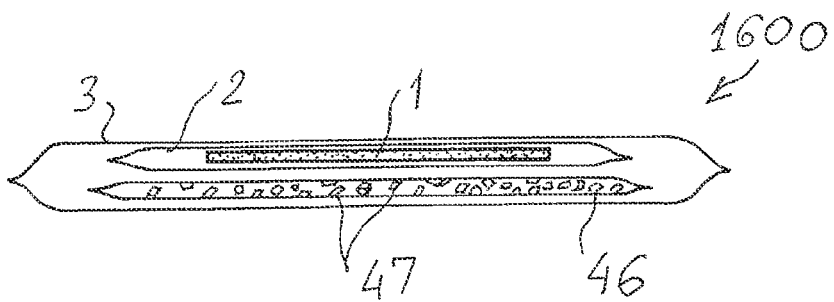
FIG. 24 A seventeenth construction form of the wound care article, with shavings in an additional internal enclosure, in a schematic side view.

The FIG. 24 represents a wound care article 1600 showing an airlaid-pad (structure 1) positioned in the internal enclosure 2 and an additional internal enclosure 46, where a casting of alginate cubes or shavings 47 is located, and both internal enclosures 2 and 46 are surrounded by the external enclosure 3. The alginate cubes or shavings 47 can be replaced by hydrofibre shavings (not represented).

Figure 25A:
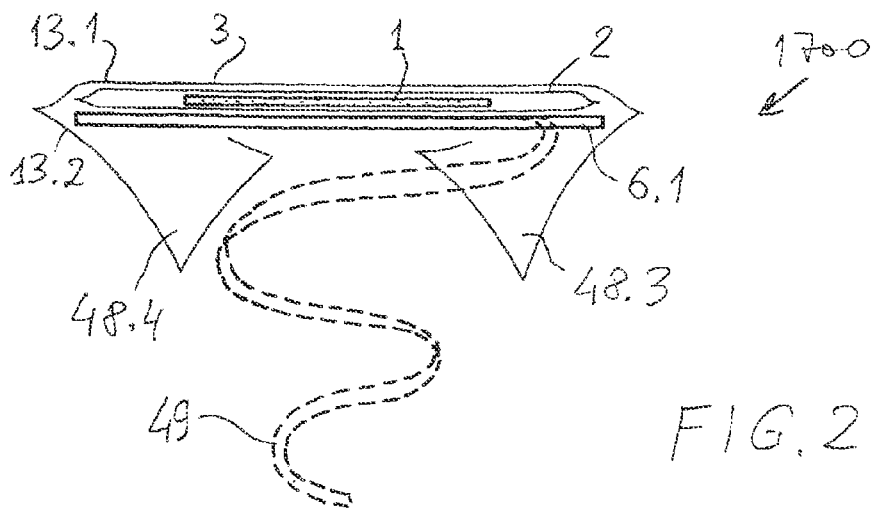
FIG. 25a An eighteenth construction form of the wound care article, with a spirally-shaped, punched material layer containing alginate, in a schematic side view.
Figure 25B:
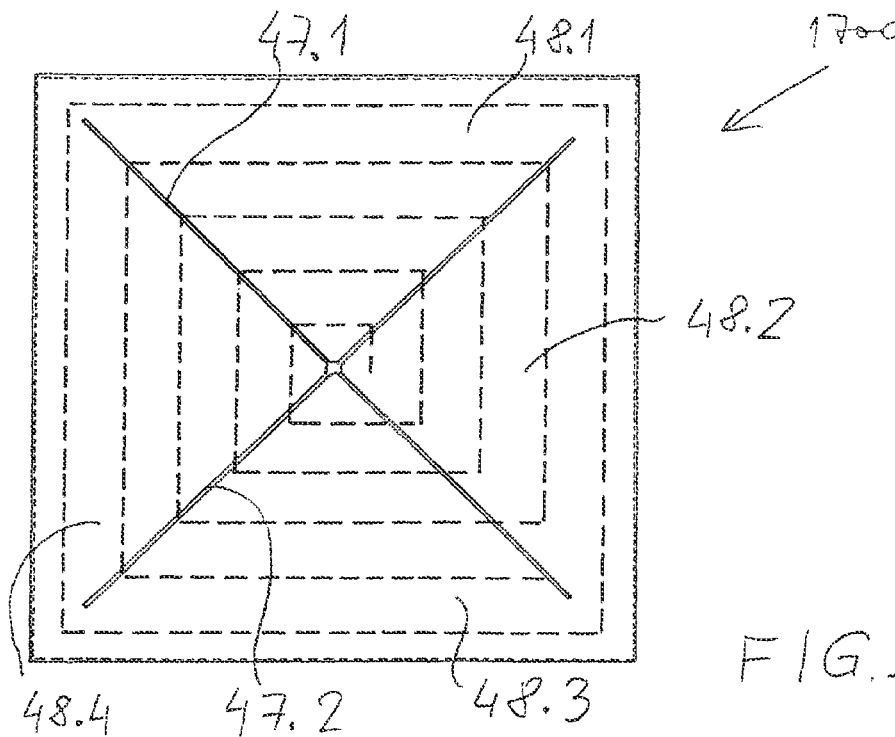
FIG. 25b The wound care article according to FIG. 25a in a top view of the side towards the wound.

The FIGS. 25a and 25b show a wound care article 1700 of similar material than the wound care article 100. The internal enclosure 2 covers the structure 1 made of an airlaid-pad, whereby the exterior enclosure 3 comprises the internal enclosure 2 with the structure 1 as well as the foam-like material layer 6.1 (polyurethane soft foam), which, however, is spirally punched, as shown FIG. 25b. On the enclosing surface 13.2 of the external enclosure 3 there are two crossing, diagonally arranged cuts 47.1, 47.2, dividing this enclosing surface in four triangular enclosing surface areas 48.1, 48.2, 48.3, 48.4, which will slightly differ from their original flat position when being used (cf. FIG. 25a) due to the gravity acting upon the spiral-shaped material layer 6.1 and thus allowing the penetration of a part of the spiral-shaped material layer 6.1 at least or of a wick 49 developed of the latter in direction towards the wound. The described wound care article 1700 thus fulfils a wick function in case of deep wounds, whereby the structure 1 above the wick 49 supports the absorbing process. In addition, there is a wound filling and healing accelerating effect. Due to the filling up of the wound, a permanent contact between absorbing materials and the wound base is ensured which guarantees a permanent exudate uptake. These advantages are also valid for all other arrangements having a convex surface and/or permitting a wound filling.

Instead of the diagonally arranged cuts 47.1, 47.2 punchings, or perforations, or markings along the drawn lines can be provided. The caretakers can cut along the lines, whereas in case of punchings or perforations the said cuts can be made by tearing.

Figure 25C:
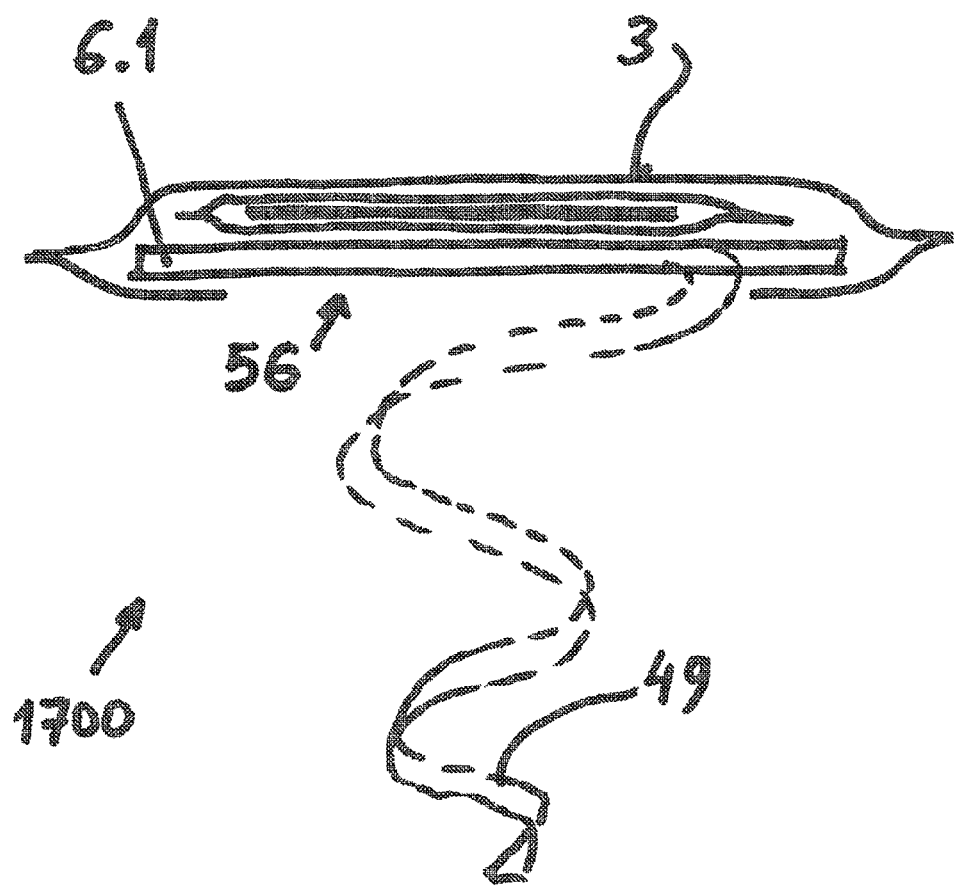
FIG. 25c A would care article including a window on the side of the enclosure which is directed towards the wound.

The FIG. 25 c shows a similar wound care article 1700, where a window 56 is provided in the enclosure on the side of enclosure 3 which is directed towards the wound, whereby the dimensions of the window are smaller than those of the material layer 6.1 provided in the external enclosure. The latter consists of spiral-shaped punched foam pad and remains in dry condition within the enclosure. Only in case of contact with liquids, especially with exudate, a part of the spiral-shaped material layer 6.1 at least or a wick 49 developed of the latter will penetrate the enclosure in direction towards the wound.

Figure 26:
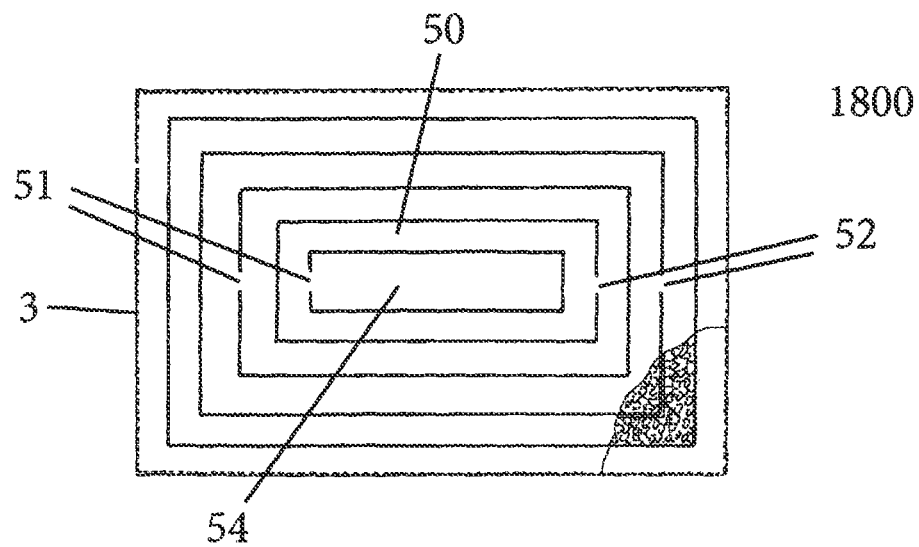
FIG. 26 A nineteenth construction form of the wound care article, with an applied material layer comprising of multiple concentric, frame-like material cuttings, in a top view of the side towards the wound.
Figure 27A:
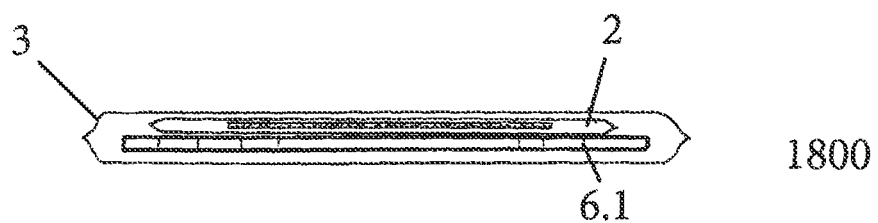
FIG. 27a The wound care article according to FIG. 26, ready for use, in a schematic side view.
Figure 27B:
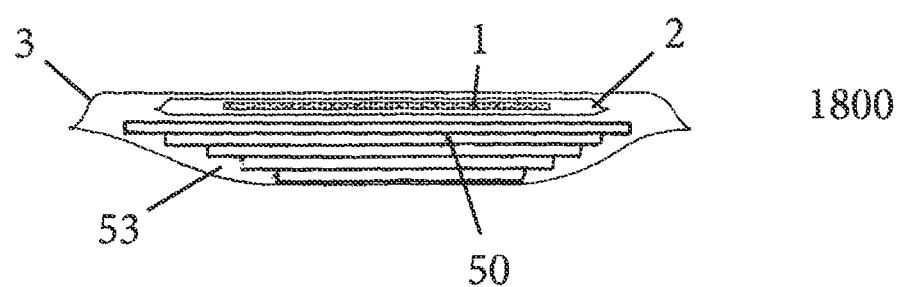
FIG. 27b The wound care article according to FIG. 26 with deformed material layer, in a schematic side view.

The FIGS. 26, 27a and 27b show a further wound care article (indicator 1800) with a likewise punched, foam-like material layer 6.1, however, being totally surrounded by the external enclosure 3 together with the pad-like structure 1 lying within the first enclosure 2.

Figure 28:
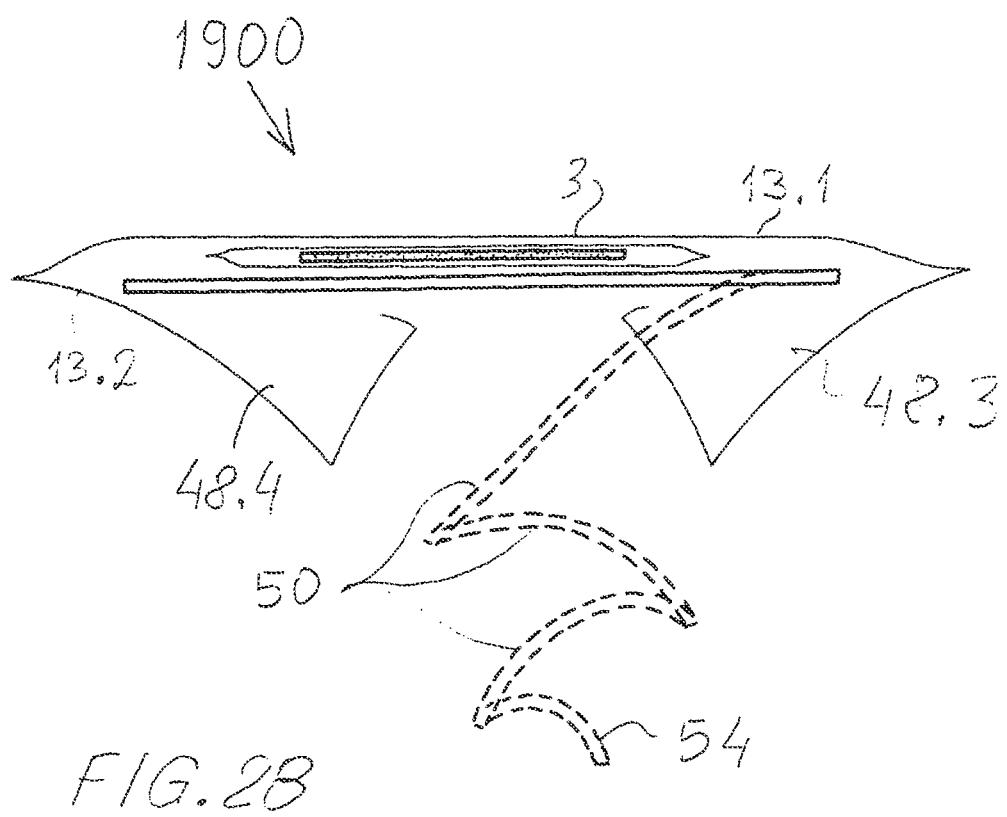
FIG. 28A twentieth construction form of the wound care article, likewise in a schematic side view.

On the rectangular material layer 6.1 multiple concentrically arranged and likewise rectangular frames 50 are punched out by means of a punching tool with bridges 51, 52 connecting the frames 50. In case of application (cf. FIG. 27b) the punched material layer 6.1 deforms to a significantly three-dimensional suction structure 53, which can adapt itself to the respective wound, if a correct size of type of the wound care article has been selected. Because the bridges 51, 52 are arranged on the material layer 6.1, the suction structure 53 does not disintegrate. Condition for the correct function of the described "Zoom-bandage" is a sufficiently extendable enclosure. If also four deformable triangular enclosing surface parts 48.1, 48.2, 48.3, 48.4 have been provided by cuts (cf. FIGS. 25a, 25b) on the enclosing surface 13.2 of the external enclosure 3, a wound care article 1900 as represented in FIG. 28 will exist. When the latter is applied on to the deep wound, the frames 50 being connected with one another through bridges will penetrate the enclosing surface 13.2. The smallest frame 50 is connected with a central material section 54 by the bridge 51 being the deepest. The wound care article 1900 is a combination of the wound care articles 1700 and 1800.

Not represented in FIGS. 25-28, but corresponding to the here described principle is a construction form, where the exterior enclosure already has a window, i.e. a cut-out, allowing to look upon the foam-like material layer underneath, punched as above described, and thus allowing the penetration of a part of the foam-like material layer 6.1 at least or of a wick 49 developed of the latter in direction towards the wound.

The FIG. 27b shows a further wound care article (indicator 1800) in an alternative arrangement, whereby multiple layers of a not punched foam-like material layer 6.1 of different sizes are arranged above each other in cascaded or pyramidal form and are completely surrounded by the external enclosure 3 together with the pad-like structure 1 lying in the first enclosure 2.

This configuration can correspond to the surface property of a deep wound, fill it up, and thus accelerate the healing process. Furthermore, due to this arrangement a permanent contact between absorbing materials and the wound base is ensured, thus assuring a permanent exudate uptake.

| Reference-Number List: | |
|---|---|
| 1 | fluid absorbing structure |
| 2 | enclosure |
| 3 | enclosure |
| 4.1, 4.2 | flat side |
| 5 | super-absorbent particles |
| 6.1 to 6.4 | material layer |
| 7 | interior surface |
| 8 | exterior surface |
| 9 | perforations |
| 10 | pad |
| 11.n | material field |
| 12.1, 12.2 | enclosing sheet |
| 13.1, 13.2 | enclosing sheet |
| 14 | adhesive point |
| 15 | alginate layer |
| 16.1, 16.2 | adhesive strips |
| 17.1, 17.2 | protective strip |
| 18 | ultrasonic seal |
| 19 | opening |
| 20 | opening (v. 6.2) |
| 21 | corner |
| 22 | frame |
| 23 | insert |
| 24 | window (v. 13.2) |
| 25 | welded seam |
| 26 | exterior edge |
| 27 | edge |
| 28 | ultrasonic seal |
| 29 | vacuum tube |
| 30 | reduced pressure system |
| 31 | covering sheet |
| 32 | covering sheet |
| 33 | opening |
| 34 | outline |
| 35 | wound |
| 36 | shavings |
| 37 | ultra-welded seam |
| 38 | periphery |
| 39 | adhesive surface |
| 40 | occlusive system |
| 41 | folds |
| 42 | bandage booklet |
| 43.1, 43.2 | wing |
| 44 | double covering |
| 45 | additional enclosure |
| 46 | additional enclosure |
| 47.1, 47.2 | cut |
| 48.1, 48.2 | enclosing surface section |
| 48.3, 48.4 | enclosing surface section |
| 49 | wick |
| 50 | frame |
| 51, 52 | bridge |
| 53 | three-dimensional absorbing structure |
| 54 | material section |
| 55.1, 55.2 | spot joint |
| A | distance |
| X | fold line |
| 100; 200; 300 | wound care article |
| 400; 500; 600 | wound care article |
| 700; 800; 900 | wound care article |
| 1000; 1100 | wound care article |
| 1200; 1300 | wound care article |
| 1400; 1500 | wound care article |
| 1600; 1700 | wound care article |
| 1800; 1900 | wound care article |

Appendix 1: Published Content of Patent DE 102006047041 (Priority Application)

Surface Area Absorbing Structure

The invention concerns a surface-area absorbing structure for application to human as well as to animal body surfaces, especially for extraction and control of wound fluids, such as pathological wound exudate from the depth of the wound base; this wound exudate causes the formation of humidity present in the wound region, due to evaporation processes of the aqueous portions of the extracted exudate; comprising:

at least one fluid-absorbing pad with a uniform coloured surface, a quantity of super-absorbent particles, which are distributed on or in the pad, and which accelerate absorption of wound exudate, and at least one liquid-permeable enclosure surrounding the pad, comprising two surfaces, whereby the super-absorbent particles are essentially white or naturally coloured.

An absorbing structure of the type mentioned initially is known from the publication "Wund Forum" by the company Paul Hartmann AG, 4/95. The absorbing structure represents a pillow-shaped wound covering employable for wet therapy, or a rinsing structure. The known absorbing structure is activated with a quantity of electrolytic solution, such as Ringer's saline solution, and applied to the wound. Through absorption of the Ringer's saline solution, the absorbing structure swells up. It has now been shown that a significant part of the existing absorbing power of the absorbing structure is lost through the use of Ringer's saline solution. In addition the healthy skin areas bordering the wound may tend to inflammatory oedema because of the permanent wetness, since a pre-saturation and a weakening of the absorptive performance occurs through filling with aqueous media and especially with its electrolytes.

The purpose of the invention is to extend the use areas for wound healing of the absorbing structure of the type initially mentioned, in particular for strongly secreting, infected wounds, from which the wound exudate may be extracted more effectively from the depth of the wound base, whereby a visual check of the emitted wound fluids stands prominent.

This purpose is solved by a corresponding type of absorbing structure, for which after application to the wound and direct moistening with the wound fluid, the pad marks the respective wound areas and the exterior contour of the wound in colour through the retention of the pad's originally-coloured surface areas, whereby the pad reaches past the respective wound edge in the applied condition of the absorbing structure, and covers healthy skin areas all around the wound, the pad changes in thickness in such a manner, in that the thickness increases proportionally corresponding to the local absorption conditions, through osmotic or atmospheric pressure conditions, whereas the original thickness of the pad remains unchanged for the mentioned adjoining surface areas.

The absorbing structure is essentially applicable on the respective wound surface in a dry condition that is not influenced by foreign, non-bodily liquids.

In the present case, the adjective "dry" designates the condition in which the absorbing structure comes to be used, as it is removed from the package under normal ambient conditions. These normal ambient conditions can correspond to the especially for human medicine recommended room temperature, and a relative humidity of the ambient air from 45% to 55%, whereby deviations from these values within broad limits are possible, for example, up to 90% for relative humidity.

In contrast to the known types of moist therapy, the absorbing structure according to the invention can be used without being wet. Here as well it can be used as covering, as a wound covering, or as a bandage.

The absorbing structure should be used for the extraction and control of wound fluids, such as pathological wound exudate from the depth of the wound base, so that the formation of humidity develops in the wound region, due to evaporation processes of the aqueous portions of the extracted exudate.

The absorbing structure according to the invention should find use for acute and chronic wounds, iatrogenically separated locations of the skin, burn wounds, inflammatory moistening processes of the skin, or ulcerating processes of neoplastic origin, moistening infections, fistulae, post-operative drainages, stomata, atopisch variable areas of the skin, refolding skin wrinkles near joints such as armpit or groin skin, mucous tissue surfaces in humans and in animals, as well as in combination with other bandage materials that have locally therapeutic effects, and for other applications, for which an atraumatic wound covering is indicated. Split skin removal locations, plastic coverings, abscesses, and urologic applications may be likewise noted as indications, as also proctologic applications and prophylactic use for prevention, for example, for containment of germ spreading and reduction of the transfer of germs. In particular, the functional combination with other broadly described advantages are prominent here. Applications under reduced atmospheric pressure, whether continuous or periodically controlled, electrically or manually, applications for compression therapy, or carbon dioxide baths form substantial approaches here.

Essentially two cleansing processes act upon the wound. First, the super-absorbent particles withdraw the wound exudate from the base of the wound, in which a normal physiological hydration is supported. The wound edges are stabilized and a desirable wound bed conditioning also takes place. Secondly, fewer aqueous waste products are concentrated in front of the enclosure, which adhere onto the enclosing material and are removed by exchanging the used absorbing structure. The absorbing structure according to the invention acts against a superfluous granulation of the wound. Since the pathological exudate is extracted, harmful proteases are extracted, which include, for example, MMP's (Matrix Metallo Proteases) and TIMP's (Tissue Inhibiting Metallo Proteases). Because of the active absorption processes of the harmful proteases, a secondary anti-inflammatory performance is achieved. The absorbing structure adjusts itself by means of the absorption and swelling process to the morphology of the wound region.

The pad locally impregnated with the wound fluid fills up the respective wound at least partially.

The pad may be freely movable within the enclosure.

Ideally, the swollen absorbing structure should be applied over its entire surface to the wound area. In this connection the enclosing surface away from the wound may comprise a textile or sheet material which is not or only slightly elastic, whereas the other surface near the wound is substantially more elastic.

It is desirable to have a surface area as large as possible for the super-absorbent particles distributed in the adhesive-free core, as well as the greatest possible homogeneity of the core. The super-absorbent particles embedded in the core may form essentially a uniform matrix. The super-absorbent particles may be sharp-edged, so that their surface area may be increased in comparison to spheres. The sharp-edged super-absorbent particles simultaneously improve the adherence to the textile fibres, which are preferably processed into a random or directionally oriented, mechanically solidified fleece. The textile fibres may be creased, bent, or folded fibre sections of various widths and lengths. The textile fibres may be placed at least partially around the individual super-absorbent particles, so that the bordering areas and thus the absorptive strength may be increased.

The super-absorbent particles may be of polymeric nature, for example, they may be present as networked, partially neutralized acrylic acid polymers. The super-absorbent particles may also be gelatinous or ceramic.

The super-absorbent particles may be added to a core network, present as Core-Cross-Linker (CXL), or also as Surface-Cross-Linker (SXL), or a mixture of both.

The absorbing structure may be designated as a hydroactive wound bandage, which permits the extracted liquid to evaporate again.

The employment possibilities for the absorbing structure may be extended by the addition of pharmacological materials of atomic or elementary basis, such as compounds of Zn, Ca, and Na. The pharmacological materials include for example: anti-inflammatories, antibiotics, growth factors, homeopathics, analgesics, antipyretics, and disinfectants.

The pad present in the enclosure or enclosure may be supplied with extracts of brown algae, carboxymethylcellulose, alginates, hydraulic fibres, hydro-capillaries, hydraulic gels, enzymes, compounds on the basis of ceramics, growth factors, metallic additives, for example, on the basis of silver, gold, platinum, and titanium, furthermore osmotically active substances, such as salts, sugar, proteins, or enzymes such as peroxidase for the regulation of osmotic pressure. The addition of germ-count reducing materials such as Octenidin or Polyhexamide may also be envisioned.

The reduction in the germ count by means of the physical characteristics of the bandage materials (reduces) the danger of mutations, biofilms, resistance, and infections, and improves the effectiveness of antibiotic measures through pharmacological treatments.

The pharmacological materials may be extracted and dissolved by the body's own liquids, such as by pathological wound exudate, without the use of electrolytic solutions.

For example, an effect upon sub-surface exudate pointing in the direction of the absorbing structure is achieved, changing the delivery of the emitted amount as well as the speed of the delivery. The pathologic tendency for particularly slow flow of wound fluids through the tissue, which can lead to a stasis of the wound fluid in the tissue depth, leads to cellular oedema and over-hydration of the cellular interstices, so that by means of the suction to be performed here on the external exudate the stasis is shifted towards a flow of the liquid to the absorbing structure. The over-hydration of the wound base depth is thus reduced, and its overall nutritive condition and thus its potential for healing is improved.

Essentially two cleansing processes act upon the wound. First, the super-absorbent particles withdraw the wound exudate from the base of the wound, in which a normal physiological hydration is supported. The wound edges are stabilized and a desirable wound bed conditioning also takes place. Secondly, fewer aqueous waste products are concentrated in front of the enclosure, which adhere onto the enclosing material and are removed by exchanging the used absorbing structure. The absorbing structure according to the invention acts against a superfluous granulation of the wound. Since the pathological exudate is extracted, harmful proteases are extracted, which include, for example, MMP's (Matrix Metallo Proteases) and TIMP's (Tissue Inhibiting Metallo Proteases). Because of the active absorption processes of the harmful proteases, a secondary anti-inflammatory performance is achieved. The absorbing structure adjusts itself by means of the absorption and swelling process to the morphology of the wound region.

By means of the absorption process, the absorbing structure may become so heavy that it slows the superfluous granulation by means of its own weight, and thus assists with the homogenization of the wound bed. The weight-determining element is the wound exudate itself.

Thus a bandage material is produced that to a superficial view has a homogenous surface, but because of its technical design offers a general wound-phase-specific solution.

Where a wound is necrotic, the bandage material scrubs it and rubs it away, whereby the subsequent wetting is captured by (the bandage material).

Where a wound is infected, there (the bandage material) extracts the germs, and withdraws germs, toxins, exudate, sources of inflammation, and oedema from the wound. Since the oedema and products of the inflammatory reaction support the creation of organized germ systems (called "biofilm"), this absorbing structure shortens the duration of the infection, it reduces the probability of occurrence for infection, assists synergistically with additional anti-infective measures, reduces the development or the probability of occurrence of biofilms, and thus forms an effective treatment option for germs such as MRSA (methicillin resistant *staphylococcus aureus*). In particular, the elimination of these population-endangering germs reflects strongly on the quick healing of chronic wounds for physicians in ambulant, home-bound, non-hospitalized situations, since they experience these pathogenic conditions here and may lead to possibly life-endangering, often unmanageable infections. This is also true especially for germs such as VRE (Vancomycin-Resistant Enterococci) and CA-MRSA (Community Associated MRSA).

Where a wound is in the cleansing phase, (the bandage material) actively extracts the rinsed out liquids and binds them.

Where a wound granulates and forms new cells, (the bandage material) protects them from the compounds of the pathological exudate of the neighbouring wound areas.

Where a wound is hyper-granulated, (the bandage material) retards it to the desired growth speed by its own weight and the weight of the extracted exudates.

Where a wound stops and the wound edge is located, (the bandage material) keeps the wound region free from the inflammatory oedematous processes of healthy skin.

Even where healthy tissue is located, the minimal thickness of (the bandage material) under compression bandages also assists in that the transitional edge of the bandage does not press very deeply into the patient's skin, whereas many other products are rather thick and promote line markings, impressions, or lasting pressure edges with the danger of reducing perfusion and thus resulting in skin damage.

Its minimal thickness transfers compressive force from surrounding compression bandages as well as possible, whereas according to La Place's law thicker bandages with the same compressive environment and thus with larger radius interfere with the compression into the depth to where it should be transferred, and transfer less or even uncontrollably less compression. This is particularly the case with foam bandages and thick cellulose layers, since they make this reduction here even worse by their elasticity.

The enclosure has various functions. Even though a technically not very demanding PP non-woven may be selected, it fulfils many functions, in that it allows water vapour to escape outward, after it has been allowed to enter into the absorbing structure as fluid exudate. To avoid the in-growth of tissue and vessels, it comprises perforations or pores, which are selected in their size in such a manner so that the granulated tissue of the wound, especially at the edge of the wound, cannot penetrate into the enclosure. For example, the perforations or pores present at the circumference of the enclosure can be smaller than those of the remaining enclosure surface.

The enclosure can be manufactured from natural materials, such as woven cotton or silk, or from perforated plastic sheeting or from plastic tissue. The enclosure surrounding the pad can be manufactured partly or completely from a so-called wound distance lattice, whereby the placement of its smooth or rough side is dependent on the respective purpose. The smooth side protects the wound from irritation and undesirable influences of a secondary bandage, whereas the rough side not only performs this function, but also actively scrubs the wound during movement and thus can provide a desirable chemotactic stimulus for the formation of new tissue.

In contrast to the known types of moist therapy, the absorbing structure according to the invention can be used without being wet.

At selected locations of the absorbing structure or the pad a significantly higher quantity of comparatively small, fast absorbing super-absorbent particles may be present than elsewhere, so that the function of a wound filler develops locally during the course of the absorption process.

If a wound-filling function is desired, an enclosure with surfaces of differing elasticity is offered. In particular, the surface toward the wound may comprise a larger elasticity than the opposite surface lying away from the wound.

Furthermore, the absorbing structure may be supported by at least one foam material layer, which is attached to the enclosure by means of at least one adhesive point or by a peripheral seam. The foam material layer may be open- or closed-pore, hydrophilic or hydrophobic. If closed-pore foam material is employed, then it is recommended to introduce continuous openings through the foam material.

The enclosure with the pad applied therein as well as the foam material layer may be arranged within an external, liquid-permeable encasing.

The absorbing structure according to the invention may be designated as universal, since it is suitable for various wound therapies (ulcus cruris, cut wounds, scrape wounds, inflamed wounds, burns, etc.), wound healing phases, as well as for use in collection means, such as drainages, stomata, fistulae, or other collection bags.

The possible addition of for example synthetic compounds such as tensides, or other materials named in Claims 60-65, leads to a significantly increased exudation of a wound and can be desirable. Here in particular, biocompatible and systemically or locally harmless materials should be used, so as not to disturb the complex linkages of interactions of pressure conditions, perfusion, venous removal, cellular metabolism, motility, and cellular inertness of cells such as erythrocytes and granulocytes, of the body's own or supplied growth factors, immune-relevant cells and materials, or other factors meaningful for the growth of tissue. A possible vascular dilatation in the wound region can have a favourable effect, even when it is a consequence of the addition of tensides, since the exudation of the wound region stands here in the foreground, and a deep cleansing of the wound region may occur. This also concerns the visually recognizable wound base, the causal-therapeutically relevant wound base, as well as the wound edge, tissue sections that are protected from exudation and harmful materials in that the super-absorbent granulate or other wound contact areas (such as foams consisting of PU, PE, or other polymers, cellulose, alginates, hydraulic gels, carbon compounds, silver compounds, honey, fleece materials, non-wovens, antiseptics, carriers of these materials, sheets or lipid-impregnated surfaces) fulfil this function.

These additions such as the ten sides or the other listed materials may be covalent, dissolvable, or loosely connected to other surfaces.

Some of the components may comprise various hole structures, which facilitate the interactions of the layers above. The transfer into the nearby layers is thereby facilitated in both directions, (both) additive to and extractive from the wound.

Additional advantages are achievable in combination with a foam construction within a common further, external enclosure. Two forms of wound relief are achieved:

For strong exudation, the side is applied to the wound, on which the absorbing structure shows toward the surface of the enclosure, and by means of the desired strong absorption effect, the wound care article relieves the wounded area, in that it extracts the undesirable pathologic exudate, which comprises harmful hormonal and component materials. Interstitial, intercellular, as well as cellular and also vascular spaces achieve close to a physiological irrigation, so that perfusion, arterial influx, venous recovery, and trans-membranous diffusion are optimized, and not by means of long diffusion paths which are interfered with by pathologic aqueous solutions and reactive bio-relevant enzymes. For cell growth requires the arterial influx of proteins, oxygen, as well as the contributions from vessels, nerves, and functional supports of the immune defence.

For weaker exudation, the foam side can be applied to the wound. Here the absorbing structure achieves an indirect factor for wound relief, in that it uses its absorptive strength to dry the reverse side of the foam. For this it is necessary that the foam is nearly soaked, so that the current flow through the foam is achieved through (for example) capillary effects, and develops as a gentle inflow into the absorbing structure. Here the absorbing structure dries the back of the foam and forms a secondary reservoir, which adds the capacity of the absorbing structure to the capacity of the foam, even though it does not have significant contact with the wound.

The enclosure, which surrounds the foam and the absorbing structure in this construction form may be formed from perforated PE sheeting, which comprises crater-shaped holes of uniform or differing geometry.

The principle of the individual absorbing structure according to the invention makes it possible to carry out a simplified visual check of the emitted wound exudate with the use of absorbing structures interspersed with super-absorbent particles, provided that the absorbing structure is employed in the form of set sizes adjusted corresponding to the wound.

A great advantage is that the absorbed wound exudate can take and remain at a set position in the absorbing structure, so that the surrounding skin near the wound is not attacked by the wound exudate.

To facilitate a general understanding of the functional method, it should be emphasized again:

Bandage for Local Drainage of Human Tissue Structures

Conditions of over-hydration in human tissue are found at multiple locations. For example, advanced kidney failure may be the fundamental cause of this effect, and progressive transfusion therapies may lead to systemic over-hydration.

The cases described lead primarily to a systemic over-hydration affecting the entire body. This may also be a late effect of left ventricular insufficiency, in which the blood initially slows within the left side of the heart, then in the lung, and than later in the entire low-pressure (circulatory) system. In the end, a general susceptibility to oedema then occurs.

However, the left ventricular insufficiency is initially a condition which first leads to a blood blockage in the lung and thus to a pulmonary oedema. Here a local susceptibility to oedema exists first.

Independent of the therapy for the underlying fundamental illness, the physician treats the over-hydration mentioned by increasing kidney performance, by administering diuretics, frequently high ceiling diuretics of the type Furosemides (Lasix). Here the ascending curve of Henle's loop leads to an inhibition of reabsorption, so that larger quantities of primary urine are excreted, and water is systemically withdrawn from the body, so that the oedematous fluids may be drawn back into the organism. The local over-hydration is eliminated, and when the cause of the fundamental illness is effectively treated, the patient is healed.

For the understanding of the extraction of water from the system by means of the kidney, a normal hydration at the oedemically endangered location is sought. This procedure is parallel to other causal-therapeutical steps lege artis of the initially selected therapy for lung oedemas with the developments mentioned.

The oedema in the lung is treated directly, actively, systemically, and pharmacologically.

It should now be reflected that the long-term administration of diuretics is not indicated in all cases. Even the treatment of each local over-hydration by means of diuretics is not indicated.

Such an over-hydration represents an oedema, which develops on the basis of a CVI (chronic venous insufficiency). The enclosing wall of the vein concerned becomes more permeable because of pathological processes, and considerable quantities of aqueous components initially present in the vein intrude out into the space outside of the vein. This occurs especially near the bones in the ankle joint of the leg, since the blood column in the vein begins here, and the hydrostatic pressure is highest here.

An over-hydration of the surrounding area, the healthy cells, the skin, and the cellular interstices develops. Diffusion of arterial and significant nutritious materials, as well as the removal of waste materials through the veins is limited. The cells shift to a reduced metabolic state, bio-relevant processes and delicately orchestrated metabolic steps are halted, and the cells die. A venous ulcus cruris develops, breaks out through the skin, and remains over-hydrated for the life of the patient.

The same process in the lung would be treated by means of increased kidney performance, at least if the entire lung were affected.

Treatment of this over-hydration in the lower leg with help of diuretics is not indicated, since a multitude of medical reasons is against it. This would be an intrusion into complex cardiologic systems, and since in the contrast to the pulmonary oedema acute mortal danger is not recognizable here, other methods must be found.

Independent of this it remains to state:

Other solutions must be found, to withdraw the exuded liquids in such a manner such as the kidney would do.

In contrast with this realization, therapeutic practice employs the application of bandages with comparatively low absorptive strength and unsatisfactory retention. Often foam bandages are used, which under pressure release what little water has been extracted, along with components that interfere with wound healing. The focus thus drifts to surface of the wound and is occupied with treating resulting effects and control of superficial cosmetic aspects.

Just how much the wound is actively retained by a deficiency of modern ideas remains here unclear.

It is clear, however, that the oedema in the leg tissue is treated indirectly, passively, locally, and physically.

Both therapy schemes have in common the combination of causal therapy (heart medication to strengthen the heart, and thus on the one hand treating the blood blockage in the lung, as well as wearing compressive socks to treat the emission of exuded venous fluids) and symptom treatments (diuresis for pulmonary drainage on the one hand, as well as the application of supposedly strongly absorbent bandages on the other).

Whereas the functional limitations of lung tissue are regarded as threatening, oedematous swelling of tissue near joints is held to be transitory and thus non-problematic. Here the first imbalance develops, which is understandable in a view toward vital functions and preservation of life, but this shortcut underestimates patient suffering, pain, chronic illness, costs, perhaps also loss of job, and a multitude of additional disadvantages.

Every physician knows that considerable numbers of prescribed compression socks are not worn appropriately or consistently. Here it develops that the primary function of compressing leg tissue fits into the patient's everyday life in only a few cases, since putting them on is very difficult (if at all possible), and as regarded as very unpleasant. The patient sweats in summer, and removal is also often difficult.

The physician despairs because of the patient's deficient compliance and tries to make the sense of this therapeutic treatment clear, knowing well that he will not have great success. The result is that either compression stockings are prescribed that produces too little pressure, but which are at least worn, or none at all are worn. The causal-therapeutic scheme, which for the lung lies in a medicational increase of heart performance, often fails for venous insufficiency, because this is achievable only by means of good compression therapy. If this does not take place, or not ideally, the vein will continue to exude for the long-term.

The view toward truly consistent oedema treatment presently sees only therapy with reduced pressure systems (VAC therapy), since this pulls liquids at the depth of the emission point by means of sub-atmospheric pressure conditions.

However, since this chosen therapy also has a multitude of disadvantages, which reach from high costs and immobility, to high requirements for application, up to cases of death, it is valid to look for a third scheme in addition to nephrological diuretics and vacuum-supported therapy schemes.

It would be advantageous if this were a simply usable bandage, which makes use of known physical relationships and conditions, and does without pharmacological processes.

Here it appears meaningful to select a bandage, which achieves the advantages of the sub-atmospheric (pressure) scheme, without needing to combat the disadvantages of reduced air pressure, such as perhaps the creation of air-tight and suction-tight chambers.

This succeeds by the use of significant osmotically reduced pressure conditions, which is placed in the form of an area-surfaced bandage on the wound surface, and which connects with physical laws with a new type of design.

A pad, which in the form of cellulose material is a carrier for SAP particles, preferably has a total weight of more than 300 g/m$^2$, and has more than 50% of swelling material. The binding strength would lie at 0.5 to 2 g NaCl in 0.9% solution.

By means of the desired bandage, such a high osmotic potential ($1^{st}$ force) is placed in the wound, that liquids on the wound surface are immediately absorbed. Their cohesive forces ($2^{nd}$ force) transmit these directional flow forces to neighbouring wound fluids, so that a deep-acting effect develops. In the depth of the wound, a flow direction for the surplus wound fluids is defined, and because of multiple effects, these are retained and continue.

Here the cohesive tendency of liquids and also their adhesive tendency ($3^{rd}$ force) are to be mentioned, so that actually only little of the liquid directly experiences the osmotic suction, whose directional effect yet still reaches deeply. It is to be assumed that even deep in the tissue a mechanism ($4^{th}$ force) takes place between the cells, which develops on the basis of capillary ascension, so that thereby the retention of the definition of the flow direction is supported.

The deep compressive force ($5^{th}$ force) of the permeable vein supports this effect, since it only has the peripheral exit for liquids and thus towards the skin. This would describe the fifth effective dimension, which, started by the high osmotic suction, leads to a relief of the over-hydration of the wound base.

The sum total of these factors leads to the sixth dimension. This is important for the cooperative functioning of the first five.

For this some preparation is necessary, because physical laws in connection with the current important here for the measurement of the ruling forces:

In physical terms, the cause of a current flow is always regarded as a pressure difference $\Delta p$ over the extent of the piping system. In our case, a pipe system does not exist in literal terms, but the tissue to be transited may be regarded as a closed system, in which the wound secretion must seek its own paths and channels. Here it is subject to inhibitory influences such as shear forces, flow resistance, frictional conditions, mechanical pressure differences, thrust impulses, flow strengths, changing diameters of the paths and channels, and other effective dimensions such as viscosity. Here the liquid hardly flows, but only slows seeps out. Despite its slow flow, the conditions for designating it as laminar current do not exist; however, the higher rate of flow conditions for designating it as turbulent current also do not exist.

$$\mathrm{Re} = \frac{\rho v \cdot d}{\eta}$$

Assuming that for this the Reynolds number Re (an empirical quantity which describes a relationship between impulses (propulsive forces) and dampening possible through friction) lies below the transformation limit of 2300, it is reasonable to assume that laminar flow conditions are present for untreated ulcers that develop as mentioned.

Constant conditions for flow direction and for rate of flow certainly do not exist; instead, mixtures of various laws apply, such as the Hagen-Poiseuille equation $$j = \frac{\pi r_0^4}{8\eta l}\Delta p$$

(describing the volume flow $\dot{V}$, i.e. the volume V per unit of time, which in laminar current flow of a viscous liquid through a capillary tube with radius r and length l) or Bernoulli's law $$w_{ges} = w_{pot} + w_{kin} = p + \frac{1}{2}\rho v^2$$

(the total pressure is the sum of the static pressure p and the dynamic pressure build-up) or by the influence of the Fåhraeus-Lindquist-effect (influence of the vessel diameter, axial migration).

In connection with this rather pure physical overview of flow conditions, it is important that in the untreated wound area various phases, conditions, pressures, and flow rates exist. Static regions neighbour upon dynamic ones, and uniform alignment is not found.

Here the above five forces finally come together, for the osmotic potential of the SAP breaks through this disorder and creates a directional definition for the wound fluid, in that it absorbs from the surface and deep wound liquids are extracted by means of the sum total of the forces named. The impulse upon the first water molecules into the inside of the bandage generates an impulse for all closely following water molecules, in that they are attached in chains with one another by means of the forces mentioned or also by means of "van der Waals" forces. The pull on the first link creates a pull on the last link, and in the sense of an independent, dynamic continuation of these processes, the water molecules follow this flow lastingly once it is started, since the osmotic downward gradient of the SAP creates a one-way street inside the product.

Imagined illustratively, an absorbing structure develops, which takes advantage of the mechanisms by means of which (for example) petrol tanks may be emptied with the help of hoses, in that a hose is inserted in the tank, briefly sucked upon, and then the petrol can be directed into a lower placed canister. Laws of gravitation and cohesion apply here, whereby in our case the downward gradient of osmotic force and cohesion applies. For the understanding of these processes, a drain develops in the tissue depth, directly within the spatial neighbourhood of the failed vein where the fluid is emitted. The bandage placed on the wound surface has its primary functional purpose exactly in this tissue depth, withdraws fluid there, and dehydrates the oedema. For this it acts through the tissue lying between the wound bed and wound base and sucks up perivenous trans-tissue over-hydration, without particularly standing in physical proximity of it. Just as a towel suck a puddle dry when a corner of it is placed in a small puddle, the high osmotic potential withdraws the sub-surface oedemas from the wound. Gently and mild to the body, and especially without dehydrating cells or the air, the extent of the exudate flow through these channels regulates the absorptive force, in that for high quantities of exudate the product jumps in actively and turns rather toward the surface of the wound base, but for lower quantities of humidity will weaken by means of evaporation processes. In all cases, the principles of moist-therapy are respected and supported.

Thus a suction bandage is created, which in the context of the functional method of a vacuum cleaner using high osmotic pressure, gently but actively removes bio-relevant noxious substances such as germs, toxins, proteases etc. Here the pathologic exudate is less a problem of being worthwhile of conquering and damaging healing, rather it becomes the opposite: an article promoting healing. It forms the transport media for the cleansing absorption effect, and after entry into the bandage is released to the wound as humidity again, once it has been freed of its damaging substances, since these do not evaporate, but rather remain in the bandage. The bandage thus cleans parts of the exudate, after it has carried itself and other damaging items into the bandage.

It has found the path into the inside of the bandage, because it was encouraged to flow in a predefined direction. This dynamic effect on rather static fluid in an area that can be reached only through surgery and within the cellular interstices leads to the formation of flow channels and thus to the relief of the perivenous tissue. In the course if these processes the pathologic exudate opens the wound surface and the wound depth for rinsing solutions and keeps the flow channels open through continuous flow.

In contrast to the VAC therapy mentioned above, the maximum absorptive performance is gradually and locally reduced over the duration of the application, and is thus not static in a manner such as electrically operated pump pressure, and therefore also less dangerous. The required absorptive strength of the bandage, which is achieved by means of the SAP, is reduced and determined by the extent of the areas of the existing exudation, so that here may be spoken of a suction strength that is adapted to the wound, and nearly even learning. Depending on the wound healing phase and the condition of each square centimeter of the wound, an absorptive performance develops that is typical for the respective wound situation.

It is astounding that the advantages of the vacuum-drawing VAC therapy is called so significant in the literature, but it still has not been said, why the therapy success is so innovative. It is the imposition of a directional definition for flow directions, the pull on deeply placed liquids, which promotes the inflow of materials promoting wound healing. To achieve the same effect by non-atmospheric reduced pressure, which is produced by means of greatly reduced osmotic pressure, seems to be a logical consequence of this realization, especially because of its advantages in respect to costs and patient safety.

In addition condition applies that in contrast to the VAC therapy, the bandage eliminates the rinsed-out germs and the perhaps infectious exudate directly after extraction from the body, and fights the germs immediately after they flow into the bandage, without their being directed into a canister, whereas no anti-microbial additives are as yet present in the channelling hose and the can. This endangers personnel, and in particular cases, endemically or epidemically relevant germs may be disposed of only as expensive and cost-intensive infectious liquid waste.

The immediate proximity of the carrier of the osmotic potential, which is created by means of the thin encasing toward the wound base, brings this pulling force to its purpose.

This also permits another significant difference to other bandage materials to become clear. For if these bandages, especially comprising cellulose wool, fluff, or fleece material, come in contact with exudates, they immediate lose their structural integrity and degenerate to soaking. Already shortly after making contact with exudate, such a bandage is wet and has lost its suction and pulling force, which already was comparatively low when it was manufactured. In the face of the necessity of extracting from the tissue depth, the appropriateness of such a bandage as bandage material for a venous ulcus cruris may be called into question. With the realization that similar illnesses may be treated with modern, hydro-active bandages such as polyurethane foams, it may be seen that here a step forward has been taken, but in fact one that does not go far enough.

For exudate and germs form the breaking points for healing. Exudate supports germs, and germs lead to exudate. Oedemas lead to reduced immune response, and the vicious circle is closed. If this circulation is broken, the wound will close.

These thoughts reflect in particular that wounds are not homogenous and the same at every point. Many wounds simultaneously experience all phases of wound healing, in that here they are necrotic and dead, there infected and covered, here exuding and watery, there fibrous, and here again hyper-granulated. Here the wound edge, there an inflammation, here fresh epithelial tissue, and there a bloody lesion due to painful removal of adhered bandages.

The automatic adaptation to these respective conditions succeeds by means of the bandage described here, because it corresponds with each of the wound situations mentioned, in that it delivers the correct response at each location. Necrotic regions are softened by means of humidity and scrubbed, germs are extracted along with the exudate of the regional inflammation, coatings are concentrated onto the external enclosing surface and are removed along with the bandage when it is removed, aqueous exudate is withdrawn with a high retention force, hyper-granulation is slowed by the bandage through its own weight and the weight of the extracted exudate, fresh epithelium is protected from the exudate and adhesion does not take place, and when it does, then a typical wound separation lattice may be used as primary bandage.

All typical advantages are optimized yet more, in that the bandage has full-surfaced contact with the wound. Here it is appropriate to reflect that the surface of a wound is not smooth like a pane of glass, but rather comprises an extremely non-homogenous morphology. From the perspective of a small cell, a comparison with an aerial view of Germany is thoroughly appropriate: in the south we have mountains, above there rather flat space, many tall buildings stand in metropolitan areas, and there lie many lakes, and also perhaps once something under sea level. The realization that hardly any wound comprises just one healing phase and only one healing situation, leads to the necessity of a bandage, which appropriately treats multiple phases simultaneously. This is ensured by the selected technical scheme.

It may be recommended to use one of the mentioned foam bandages as the full-surfaced primary contact layer, so long as the advantages of the absorbing structure find additional use. This could occur in that the foam has contact with the wound, and the absorbing structure is applied directly on the reverse, first to ensure the adjustment to a very non-homogenous wound base morphology by means of a foam, which as flow-through and contact structure transfers the wound fluids directly in the absorbing structure. It is also conceivable to fulfil this function by means of alginates, carbon bandages, or cotton and fleece materials.

When PU foams are used, these tend to roll up at their edges. The use of an absorbing structure on the reverse creates a desirable mechanical counter-force here, and contributes to retaining full-surfaced contact area.

The exterior form of the bandage may exist in the form of squares or other geometries, but may also have anatomic forms such as (for example) gloves for the treatment of extremities.

Of primary importance in all cases is that a new understanding develops for wound treatment, oedema therapy, and treatment of vascular insufficiency, in that emitted venous liquid, oedemas and their liquids are made dynamic and directed to the skin surface, to be powerfully withdrawn there, so that the wound can close. De-stressing, swelling reduction, damming, and the withdrawal of damaging materials lead to relief, deep recovery, and tissue de-blockage, which is cleansed from the deep perivenous tissue up to the wound base by means of this rinsing process.

This new understanding also contains the option of being combinable with VAC therapy, to achieve a strengthening of the suction performance. Modifications are conceivable, by means of which reduction of the air suction is made possible, since osmotic suction performance is added to it, and thus permit regulating synergetic factors.

In all cases, with or without VAC, the body exudates and waste products, which are carried into the absorbing structure by means of the rinsing effect, are collected.

Synergetic factors may also have reciprocal effects, for example, in cases where for example the exudate is encouraged and increased by means of tensides, the use of the absorbing structure is necessary to control the aroused exudation.

Other additives may also be natural materials, for example, extracts of fruits or nuts, to be mentioned here are in particular saponins, the extracts of "soap nuts".

The swelling materials may lead to a reduction of the germ count in the wound region by means of ion exchange processes, in that depolarization and its transfer is obstructed, or in that concentration gradients at the cell membranes of organisms and germs are reduced. Here the treatment of resistant germs may play an endemic or epidemic role, for the colonized wound often supports the germs and the germs often support the wound. The breaking of this (cycle) is a considerable measure for containing the spread of germs and their infections.

The possibility of depositing super-absorbent granulate in a bed of cut and folded cellulose fibres, before they swell, plays a considerable role here for the production of humidity in the wound area, because the desired maximization of surface area is thereby achieved. Covering layers comprising cellulose, high surface area granulate, and surface-area-intensive fibres lead in concert to much space and much surface area for the evaporation of retained fluid components, and thus for the production and maintenance of desirably moist wound environments.

This form of pad as SAP carrier exists in particular as the (so-called) "airlaid" type.

Non-systemic, local, but necessary drainage, such as diuretics and the kidney would provide for the lung, are thus effected by means of an exudate-hungry bandage comprising with high osmotic potential. For it is not acceptable that skin and connective tissues must die, merely because a vein should fail.

For only by means of these rinsing processes is it conceivable to transport impurities, germ remains, cellular remains, metabolic products of bacteria, and cells present in the wound region to the surface, thus to absorb them directly there and to remove them in a controlled manner.

Appendix 2: Claims of the Patent DE 102006047041 (Priority Application)

An surface-area absorbing structure (100; 101; 102; 103) for application to human as well as animal body surfaces, especially for extraction and control of wound fluids, such as pathological wound exudate from the depth of the wound base, which wound exudate the formation of humidity present in the wound region because of evaporation processes aqueous sections of the extracted exudate caused, comprising:
at least one fluid-absorbing pad (1; 11; 21) with uniform colour surface,
a quantity of super-absorbent particles (20), which are distributed on or in the pad and which accelerates the absorption of wound exudate,
and at least one the pad (1; 11; 21) surrounding, at least partly liquid-permeable enclosure (10),
whereby the super-absorbent particles (20) are essentially white or naturally coloured,
characterized in that:
after application to the wound (30) and direct moistening with the wound fluid, the pad (1; 11; 21) marks the respective wound areas (34) and the exterior contour (31) of the wound in colour through the retention of the pad's originally-coloured surface areas (33), whereby the pad (1; 11; 21) reaches past the respective wound edge in the applied condition of the absorbing structure, and covers healthy skin areas all around the wound,
and that the pad (1; 11; 21) changes its thickness (D) in such a manner, that the thickness increases proportionally corresponding to the local absorption conditions related to osmotic or atmospheric pressure; whereas the original thickness (D) of the pad remains unchanged for the mentioned adjoining surface areas (33).

2. The absorbing structure according to claim 1, characterized in that it serves for:
placement on human and animal surfaces, and for mounting on surfaces of chronic and acute wounds,
reduction of over-hydration in peripheral tissue layers, which have contact with the ambient air,
reduction of over-hydration in covered and deeper tissue layers, which do not have contact with the ambient air and comprises at least a quantity of osmotically active swelling material such as super-absorbent granules, and
in the absorbing structure a quantity of materials is present, which have influence to reduce germ count,
at least portions of the swelling materials have a lower retention and binding strength for water than its vapour pressure and steam pressure are, and therefore moist wound conditions can be created from extracted liquids,
the osmotic pressure of the absorbing structure before use can bind more than 0.3 g of 0.9-% NaCl solution per square centimeter, because of the selection and quantity of the swelling materials, so that the hydrostatic counter-pressure in spatial proximity to tissue structures losing bodily fluids in pathologic dimensions is reduced through cohesive forces and osmotic pressure differences for covered tissue layers, whereby the oedematous compression and the over-hydration of bodily tissue is reduced.

3. surface-area absorbing structure for use with chronic non-homogeneous wounds, especially to dissolve and to absorb germs anchored on the wound surface and/or in the wound base, comprising:
at least one fluid-absorbing fleece pad (1; 11; 21),
A quantity of super-absorbent particles (20), which are distributed on or in the fleece pad and accelerate the absorption if pathological wound exudate,
and at least one enclosure (10) surrounding the fleece pad (1; 11; 21) that is at least partially liquid-permeable, characterized in that the absorbing structure is applicable on the respective wound surface in a dry condition that is not influenced by foreign, non-bodily liquids after application to the wound (30) and direct moistening with the wound fluid, the fleece pad (1; 11; 21) intrudes into the respective wound areas (34) at least locally and produces a suction on the wound surface, which acts with an osmotic pressure in the wound base directed toward the wound surface, and which the germs present there are continuously rinsed out by means of enclosed wound exudate, and are transported into the fleece pad (1; 11; 21) enriched with super-absorbent particles (20) by means of the perforations on the enclosure (10), in that the steam pressure of the aqueous portions of the wound exudate are higher than the retentive strength of the selected super-absorbent particles (20).

4. The absorbing structure according to claim 1, characterized in that
the fleece pad (1; 11; 21) reaches past the respective wound edge in the applied condition of the absorbing structure, and covers healthy skin areas all around the wound,
and that the pad (1; 11; 21) changes its thickness (D) in such a manner, that the thickness increases proportionally corresponding to the local absorption conditions related to osmotic or atmospheric pressure; whereas the original thickness (D) of the pad remains unchanged for the mentioned adjoining surface areas (33).

5. The absorbing structure according to claim 1, characterized in that the enclosure (10) is encircled by a seam (6), which defines a first surface (F1), which is at least 5% larger than a second surface (F2) defined by an outline (U) of the pad.

6. The absorbing structure according to claim 4, characterized in that corresponding to pressure conditions on the wound permitting, the seam (6) is a long-lasting deformable ultrasonic weld seam.

7. The absorbing structure according to any of the preceding claims, characterized in that the absorbing structure is covered or supported on at least one of its surfaces by at least one alginate or foam pad (41).

8. The absorbing structure according to claim 5, characterized in that the alginate or foam pad (41) is peripherally attached to the enclosure (10).

9. The absorbing structure according to claim 5, characterized in that the alginate or foam pad (41) is affixed to the enclosure (10) by means of at least one adhesive point (42) or adhesive line.

10. The absorbing structure according to one of the claims 5 to 7, characterized in that the enclosure (10) with the therein applied fleece pad as well as the alginate or foam pad (41) within an external, additional liquid-permeable encasing (43) arranged are.

11. The absorbing structure according to any of the preceding claims, characterized in that it generates an osmotic pressure for fluid flow directions from the wound base peripherally to the skin, which in total with the oedematous hydraulic pressure in the same direction, creates a dynamic flow direction from the wound base into the inside of the absorbing structure, so that the wound fluids enter the visually recognizable wound base, which has contact to the ambient air, and upon which the absorbing structure is applied, without remaining statically on it in the form of oedema-producing accumulations, but instead remain bound in the absorbing structure in the form of water vapour and humidity, and remain in the wound region until the bandage is exchanged.

12. The absorbing structure according to any of the preceding claims, characterized in that the absorbing structure generates an osmotic pressure for fluid flow directions from the wound base peripherally to the skin, which in total with the oedematous hydraulic pressure in the same direction, creates a dynamic flow direction from the wound base into the inside of the absorbing structure, so that the wound fluids enter the visually recognizable wound base, which has contact to the ambient air, and upon which the absorbing structure is applied, and enter into the absorbing structure, whereby in relationship with rinsing processes and traction it rinses its germs and impurities from the wound surface into the inside of the absorbing structure, so that this suction acts against the stability or even the increase of germ counts.

13. The absorbing structure according to any of the preceding claims, characterized in that the absorbing structure produces by means of the swelling process a relative depletion of electrolytes such as potassium, calcium, magnesium, etc. in the absorbed liquids in the space within the enclosure (10), whereby environment-dependent or concentration-dependent mechanisms (such as depolarization, cell wall stability of germs, or gradients in the electronegativity for microbes such as bacteria, fungi or their spores in only limited development) occur to attack the microbes, so that for example, bacteriostatic or bactericidal influences develop.

14. The absorbing structure according to claim 1, characterized in that the absorbing structure is applicable on the respective wound surface in a dry condition that is not influenced by foreign, non-bodily liquids.

15. The absorbing structure according to claim 1, characterized in that the pad (1; 11; 21) locally impregnated with the wound fluid at least partially fills the respective wound.

16. The absorbing structure according to claim 1 or 2, characterized in that the absorbing structure is covered or supported by a perforated material section that protects the wound, or is attached or peripherally connected to one such (material section).

17. The absorbing structure according to any of the preceding claims, characterized in that the pad (1) comprises a core layer (3) and at least one enclosing sheets (12.1, 12.2).

18. The absorbing structure according to any of the preceding claims, characterized in that the super-absorbent particles (20) are present in the core layer (3) as distributed cellulose fibres, which core layer (3) is contained by two enclosing sheets (12.1, 12.2) of cellulose.

19. The absorbing structure according to any of the preceding claims, characterized in that the material containing cellulose comprises random fleece, whose fibre sections (13) wrap at least partly around the super-absorbent particles (20).

20. The absorbing structure according to any of the preceding claims, characterized in that the absorbing structure comprises a differing, material-dependent absorptive performance on each of its two sides.

21. The absorbing structure according to any of the preceding claims, characterized in that the pad (11) comprises two layers (7.1, 7.2) that are stacked on top of each other or folded together, between which the super-absorbent particles (20) are arranged.

22. The absorbing structure according to any of the preceding claims, characterized in that the pad (11) comprises two layers (7.1, 7.2) that are stacked on top of each other or folded together, at least one of which is distributed with a quantity of super-absorbent particles (20).

23. The absorbing structure according to any of the preceding claims, characterized in that the layers (7.1, 7.2) are separated from one other by a dividing wall (32).

24. The absorbing structure according to claim 11, characterized in that the dividing wall (32) is impermeable to liquids.

25. The absorbing structure according to claim 12, characterized in that the dividing wall (32) is perforated.

26. The absorbing structure according to claim 12, characterized in that at least one surface of the absorbing structure, for example, the dividing wall (32), is impermeable to liquids, but permeable to water vapour.

27. The absorbing structure according to any of the preceding claims, characterized in that the super-absorbent particles (20) are arranged over the surface on at least one of the upper sides (14.1, 14.2) of the pad.

28. The absorbing structure according to any of the preceding claims, characterized in that at least one location of the absorbing structure a significantly higher quantity of comparatively small, fast absorbing super-absorbent particles (20) is locally present than elsewhere, so that the function of a wound filler develops locally during the course of the absorption process.

29. The absorbing structure according to any of the preceding claims, characterized in that bio-relevant materials of atomic or elementary basis, such as perhaps silver compounds, growth factors, activated charcoal surfaces, antiseptics, tensides, and carrier substances for these materials are added to the pad (1).

30. The absorbing structure according to any of the preceding claims, characterized in that the enclosure (10) is surrounded by a seam (6), which defines a first surface (F1), which is at least 5% larger than a second surface (F2) defined by an outline (U) of the pad.

31. The absorbing structure according to claim 18, characterized in that the seam (6) is an ultrasonic welded seam that is flexible, and remains deformable according to the pressure conditions on the wound.

32. The absorbing structure according to any of the preceding claims, characterized in that the pad or core layer (3) and/or enclosing sheets (12.1, 12.2) are woven in form.

33. The absorbing structure according to any of the preceding claims, characterized in that the pad is of "airlaid" type.

34. The absorbing structure according to any of the preceding claims, characterized in that the absorbing structure is covered or supported on at least one of its surfaces by at least one foam material layer (41).

35. The absorbing structure according to claim 22, characterized in that the foam material layer (41) is peripherally attached to the enclosure (10).

36. The absorbing structure according to claim 22, characterized in that the foam material layer (41) is affixed to the enclosure (10) by means of at least one adhesive point (42) or an adhesive line.

37. The absorbing structure according to one of the claims 22 to 24, characterized in that the enclosure (10) with the therein applied pad as well as the foam material layer (41) are arranged within an additional, liquid-permeable external encasing (43).

38. The absorbing structure according to any of the preceding claims, characterized in that the pad (1; 11; 21) is freely movable within the enclosure (10).

39. The absorbing structure according to any of the preceding claims, characterized in that the pad (1; 11; 21) is affixed within the enclosure (10).

40. The absorbing structure according to any of the preceding claims, characterized in that the surfaces (2.1, 2.2) of the enclosure or its contents comprise different elasticities.

41. The absorbing structure according to claim 28, characterized in that the surface (2.1) near the wound comprises a larger elasticity than the other surface (2.2).

42. The absorbing structure according to claim 28, characterized in that at least one surface, for example, the surface (2.2) away from the wound, comprises an insignificant elasticity approaching or equal to the zero value.

43. The absorbing structure according to any of the preceding claims, characterized in that the enclosure (10) comprises a border hem (9), in that the seam (6) does not lie on the outermost circumference of the enclosure (10), but rather leaves a gap (15) in the enclosing material.

44. The absorbing structure according to any of the preceding claims, characterized in that surface-active substances, which have an affinity for germ surfaces are added to the absorbing structure.

45. The absorbing structure according to any of the preceding claims, characterized in that the absorbing structure comprises an extractive capacity that is at least 50 g of water per 100 cm$^2$ of the pad's (1; 11; 21) surface, measured according to DIN 53923.

46. The absorbing structure according to any of the preceding claims, characterized in that the absorbing structure is a hydro-active wound bandage, which permits extracted liquid to evaporate.

47. The absorbing structure according to any of the preceding claims, characterized in that the super-absorbent particles (20) are composed of sodium acrylate/acrylic acid polymerisations.

48. The absorbing structure according to any of the preceding claims, characterized in that the super-absorbent particles (20) are ceramic.

49. The absorbing structure according to any of the preceding claims, characterized in that the enclosure (10) comprises weight of at least 15 g/m$^2$, preferably 25 g/m$^2$ to 35 g/m$^2$.

50. The absorbing structure according to any of the preceding claims, characterized in that odour-limiting materials, such as activated charcoal, are added to the absorbing structure.

51. The absorbing structure according to any of the preceding claims, characterized in that bactericidal materials, such as silver compounds, are added to the absorbing structure.

52. The absorbing structure according to any of the preceding claims, characterized in that additives that fall under medical regulations are supplied to the absorbing structure, for example, mineral corticoids, proteases, antibiotics, anti-inflammatory agents, antipyretics, analgesics, anticonvulsive additives, or growth factors.

53. The absorbing structure according to any of the preceding claims, characterized in that the absorbing structure is part of a compression system or of a reduced pressure system.

54. The absorbing structure according to any of the preceding claims, characterized in that the absorbing structure is part of a post-operative drainage system.

55. The absorbing structure according to any of the preceding claims, characterized in that the absorbing structure is part of an occlusive or semi-occlusive bandage.

56. The absorbing structure according to any of the preceding claims, characterized in that lipo-colloids are added to the pad (1; 11; 21) and/or the enclosure (10).

57. The absorbing structure according to any of the preceding claims, characterized in that the super-absorbent particles (20) comprises a concentration of remaining monomers that lies below 2000 ppm (units).

58. The absorbing structure according to any of the preceding claims, characterized in that the super-absorbent particles (20) comprise a pH level that is less than 9.

59. The absorbing structure according to any of the preceding claims, characterized in that the super-absorbent particles (20) comprise a size from 0.01 mm to 0.5 mm.

60. The absorbing structure according to any of the preceding claims, characterized in that the super-absorbent particles (20) comprise a size from 0.5 mm to 3.0 mm.

61. The absorbing structure according to any of the preceding claims, characterized in that the super-absorbent particles (20) comprise various particle sizes, for example, mixtures particles with size differences in the region of a factor of 5.

62. The absorbing structure according to any of the preceding claims, characterized in that the super-absorbent particles (20) are glued onto the pad.

63. The absorbing structure according to any of the preceding claims, characterized in that the super-absorbent particles (20) are embedded, for example pressed into in the pad.

64. The absorbing structure according to any of the preceding claims, characterized in that the super-absorbent particles (20) are sprayed onto the pad.

65. The absorbing structure according to any of the preceding claims, characterized in that the absorbing structure comprises additives, which have characteristics of ion reserves, in that on exposure to corresponding ions exchange processes occur, whereby in particular potassium as well as magnesium are bound.

66. The absorbing structure according to any of the preceding claims, characterized in that the super-absorbent particles (20) comprise a core network, present as Core-Cross-Linker (CXL) or also as Surface-Cross-Linker (SXL), or a mixture of both.

67. The absorbing structure according to any of the preceding claims, characterized in that the absorbing structure extracts the materials occurring in the wound and selectively releases the aqueous portions again, in that the vapour pressure of the water is higher than the retentive strength of the selected super-absorbent particles (20).

68. The absorbing structure according to any of the preceding claims, characterized in that the absorbing structure is to be used in the cleansing phase of the wound.

69. The absorbing structure according to any of the preceding claims, characterized in that the super-absorbent particles (20) comprise strong cytotoxic and thus bactericidal or bacteriostatic characteristics, which in the course of the absorption process are reduced or eliminated by means of the inflowing exudate and the ions contained therein, without the application of electrolytic solutions before use.

70. The absorbing structure according to any of the preceding claims, characterized in that the absorbing structure is usable as secondary construction.

71. The absorbing structure according to any of the preceding claims, characterized in that the absorbing structure is usable as primary or tertiary bandage.

72. The absorbing structure according to any of the preceding claims, characterized in that molecules or compounds from the group containing detergents, tensides, or other chemically reactive polymers are present on at least one of its surfaces.

73. The absorbing structure according to any of the preceding claims, characterized in that these detergents comprise glycol compounds containing carbon, such as PEG (polyethyleneglycol) or PPG (polypropyleneglycol).

74. The absorbing structure according to any of the preceding claims, characterized in that these detergents are chemically related with esters or ethers such as poloxamers, Meroxapol, Poloxamin, or other block polymers.

75. The absorbing structure according to any of the preceding claims, characterized in that the detergents include silicone polymers such as polyethoxylated and/or polypropoxylated silicone polymers, substituted monomers or polymers ethoxylate or propoxylate, alkylpolyglucoside (APG), or Aziridin-homopolymer (PEI, polyethylenimine).

76. The absorbing structure according to any of the preceding claims, characterized in that these detergents are long-chained, ionic (anionic such as SDS and SAS and ABS, cationic, amphoteric such as poloxamine), and/or non-ionic, such as APG and FAEO and FAPO.

77. The absorbing structure according to any of the preceding claims, characterized in that the detergent is a surfactant, or F-68 (Pluronic), or Triton X-100, or Tetronic 1307, or Surfynol 465, or Surfynol 485, or Silwet L7600, or Cremophor EL, or Tween 20, or Surfactant 10G, or a material group or type related to or associated with these materials, or a mixture of similar materials.

78. The absorbing structure according to any of the preceding claims, characterized in that a carrier, such as a pad of alginates, cellulose, honey, fleece, cotton wool, or carbon compounds is present together with the materials listed in claims 60 to 65 in an enclosure comprising at least partially of liquid-permeable material.

79. The use of an absorbing structure according to any of the preceding claims for chronic and acute wounds, for compartment syndromes, burn wounds, locations with separated dermis, and for contact with human organ systems such as intestinal, peritoneum, cavities, tumour tissue, iatrogenically supplied areas, ascites, and organ contents such as escaping intestinal contents, gall-bladder fluids, pancreatic fluids, or stomach fluids.

80. The use of an absorbing structure according to any of the preceding claims to produce or maintain moist wound conditions, whereby at least one of the absorbing structure's preceding claims may take part in the production or maintenance.

81. The absorbing structure according to any of the preceding claims, characterized in that it is present in the neighbourhood of a foam construction or an alginate pad or a carrier surface with additives such as the above, in an additional common enclosure, which has been thermally sealed, for example, by means of ultrasound, or which has been glued.

82. The absorbing structure according to any of the preceding claims, characterized in that super-absorbent particles are present at an additional location rather than in the absorbing structure itself, for example, in a foam, on a surface of the enclosure, on intermediate surfaces, or on other surfaces of the bandage.

83. The absorbing structure according to any of the preceding claims, characterized in that with increasing filling the free air regions in the enclosure gradually become filled, so the absorbing structure approaches a circular shape by means of the swelling process, and by volume and weight increase, whereby reaching the circular (shape) is strongly dependent on the seam and the product axis that results from it.

84. The absorbing structure according to any of the preceding claims, characterized in that with the flow of wound fluids into the inside of the product, cellular remains, waste products, and germs, which may perhaps be pathogens or even multi-resistant, are absorbed, whereby the germs experience ambient conditions that are hostile for their life, since dehydration, ion exchange, a deficient nutrient base, and the presence of oxygen may be significant here.

85. The absorbing structure according to any of the preceding claims, characterized in that it generates an osmotic pressure for fluid flow directions from the wound base peripherally to the skin, which in total with the oedematous hydraulic pressure in the same direction, creates a dynamic flow direction from the wound base into the inside of the absorbing structure, so that the wound fluids enter the visually recognizable wound base, which has contact to the ambient air, and upon which the absorbing structure is applied, without remaining statically on it in the form of oedema-producing accumulations, but instead remain bound in the absorbing structure in the form of water vapour and humidity, and remain in the wound region until the bandage is exchanged.

86. The absorbing structure according to any of the preceding claims, characterized in that it generates an osmotic pressure for fluid flow directions from the wound base peripherally to the skin, which in total with the oedematous hydraulic pressure in the same direction, creates a dynamic flow direction from the wound base into the inside of the absorbing structure, so that the wound fluids enter the visually recognizable wound base, which has contact to the ambient air, and upon which the absorbing structure is applied, and enter into the absorbing structure, whereby in relationship with rinsing processes and traction it rinses its germs and impurities from the wound surface into the inside of the product, so that this suction acts against the stability or even the increase of germ counts.

87. The absorbing structure according to any of the preceding claims, characterized in that the it produces by means of the swelling process a relative depletion of electrolytes such as potassium, calcium, magnesium, etc. in the absorbed liquids in the space within the enclosure (10), whereby environment-dependent or concentration-dependent mechanisms (such as depolarization, cell wall stability of germs, or gradients in the electronegativity for microbes such as bacteria, fungi or their spores in only limited development) occur to attack the microbes, so that for example, bacteriostatic or bactericidal influences develop.

End of the Appendix

The invention claimed is:

1. A wound care article capable of extracting and controlling wound fluids, comprising:
    at least one first fluid-absorbing structure, which is surrounded by a liquid-permeable, first enclosure, and a liquid-permeable second enclosure, comprising two enclosing surfaces, wherein, the first enclosure is covered or supported on at least one of its flat sides by at least one fluid-absorbing material layer, which is arranged between the first enclosure and one of the enclosing surfaces of the second enclosure, wherein the first fluid-absorbing structure is a mechanically solidified fleece-like pad, wherein the fluid-absorbing material layer is an absorbent foam material pad, and wherein the first fluid-absorbing structure and/or the fluid-absorbing material layer comprise superabsorbent material.

2. The wound care article according to claim 1, wherein the first enclosure is surrounded by the second enclosure.

3. The wound care article according to claim 1, characterized in that the fleece-like pad is supported by a pad containing alginate, arranged within the first enclosure, whereby the pad containing alginate is arranged on said fleece-like pad on the side that is turned away from the material layer.

4. The wound care article according to claim 1, further comprising an alginate layer that is covered over the material layer, whereby said alginate layer lies between the material layer and one of the enclosing surface of the second enclosure.

5. The wound care article according to claim 1, wherein the material layer is peripherally attached to the first enclosure.

6. The wound care article according to claim 1, wherein the first and/or the second enclosure comprises one rough interior surface and one smooth exterior surface.

7. The wound care article according to claim 6, wherein the rough interior surface of the first and/or of the second enclosure further comprises funnel-shaped perforations introduced into the enclosing material.

8. The wound care article according to claim 6, wherein the smooth exterior surface of the first and/or of the second enclosure comprises arched material section, extending between the perforations.

9. The wound care article according to claim 1, wherein a central opening is processed on the fluid-absorbing material layer, in which an insert containing alginate is placed.

10. The wound care article according to claim 9, wherein the insert is released for direct contact with the respective wound through a window located on one of the enclosing surfaces of the second enclosure.

11. The wound care article according to claim 1, wherein at least one of the enclosing surfaces of the second enclosure is covered by a covering sheet.

12. The wound care article according to claim 1, wherein the material layer is spirally shaped in a top view of its flat side.

13. The wound care article according to claim 1, wherein the material layer in a top view of its flat side comprises multiple, concentrically applied, round or rectangular frames.

14. The wound care article according to claim 1, wherein at least one cut is introduced on said one of the enclosing surfaces of the second enclosure, and the material layer that is spirally shaped or comprises multiple concentric frames at least partly extends out of said one of the enclosing surfaces when applied on the wound.

15. The wound care article according to claim 1, wherein the fleece-like pad contains alginate.

16. The wound care article according to claim 1, wherein the fleece-like pad contains cellulose.

17. The wound care article according to claim 1, wherein the fleece-like pad contains carboxymethyl cellulose.

18. The wound care article according to claim 17, wherein the carboxymethyl cellulose is present in the form of sodium carboxymethyl cellulose.

19. The wound care article according to claim 1, wherein the fleece-like pad is of an Airlaid type.

20. The wound care article according to claim 1, wherein the fleece-like pad is in the form of casting, a pressing, and/or in form of shavings.

21. The wound care article according to claim 1, wherein within the fleece-like pad the super-absorbent particles are arranged in the matrix containing cellulose fibres.

22. The wound care article according to claim 1, wherein the super-absorbent particles are present in powder or granulate form in a particle size between from 100 μm to about 1000 μm.

23. The wound care article according to claim 1, wherein the foam material pad is made of polyurethane foam.

24. The wound care article according to claim 1, wherein the foam material pad is made of cross-linked foams.

25. The wound care article according to claim 1, wherein the foam material is an open-pored foam material.

26. The wound care article according to claim 1, wherein the foam material pad is an closed-pore foam material with continuous openings and/or holes in the foam material.

27. The wound care article according to claim 1, wherein the at least one first fluid-absorbing structure comprises a greater absorptive capacity and a higher extractive ability than the at least one fluid-absorbing material layer.

28. The wound care article according to claim 1, wherein the foam material is an open-celled hydrophilic foam structure.

* * * * *